US005880125A

United States Patent [19]

Nargund

[11] Patent Number: 5,880,125

[45] Date of Patent: Mar. 9, 1999

[54] 4-SPIROINDOLINE PIPERIDINES PROMOTE RELEASE OF GROWTH HORMONE

[75] Inventor: Ravi Nargund, East Brunswick, N.J.

[73] Assignee: Merck & Co., Inc., Rahway, N.J.

[21] Appl. No.: 820,233

[22] Filed: Mar. 18, 1997

Related U.S. Application Data

[60] Provisional application No. 60/016,302 Mar. 21, 1996.

[51] Int. Cl.[6] ........................ A61K 31/44; A61K 31/495; C07D 401/14; C07D 403/14

[52] U.S. Cl. .......................... 514/253; 514/255; 514/256; 514/278; 544/80; 544/81; 544/120; 544/121; 544/122; 544/336; 544/359; 546/17

[58] Field of Search ............................... 546/17; 514/278, 514/253, 255, 256; 544/80, 81, 120, 121, 122, 359, 336

[56] References Cited

U.S. PATENT DOCUMENTS

| | | | |
|---|---|---|---|
| 5,492,916 | 2/1996 | Morriello et al. | 514/318 |
| 5,492,920 | 2/1996 | Chen et al. | 514/323 |
| 5,494,919 | 2/1996 | Morriello et al. | 514/323 |
| 5,536,716 | 7/1996 | Chen et al. | 514/215 |
| 5,559,128 | 9/1996 | Chakravarty et al. | 514/323 |
| 5,578,593 | 11/1996 | Chen et al. | 514/212 |

FOREIGN PATENT DOCUMENTS

| | | |
|---|---|---|
| WO 96/02530 | 2/1996 | WIPO . |
| WO 96/13265 | 5/1996 | WIPO . |
| WO 96/35713 | 11/1996 | WIPO . |
| WO 96/38471 | 12/1996 | WIPO . |

*Primary Examiner*—Alan L. Rotman
*Attorney, Agent, or Firm*—J. Eric Thies; David L. Rose

[57] ABSTRACT

The present invention is directed to certain novel compounds identified as 4-spiroindoline piperidines of the general structural formula:

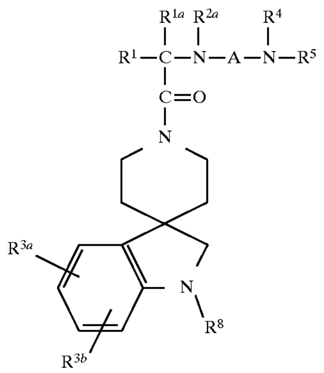

wherein $R^1$, $R^{1a}$, $R^{2a}$, $R^{3a}$, $R^{3b}$, $R^4$, $R^5$, $R^8$, and A are as defined herein. These compounds promote the release of growth hormone in humans and animals. This property can be utilized to promote the growth of food animals to render the production of edible meat products more efficient, and in humans, to treat physiological or medical conditions characterized by a deficiency in growth hormone secretion, such as short stature in growth hormone deficient children, and to treat medical conditions which are improved by the anabolic effects of growth hormone. Growth hormone releasing compositions containing these compounds as the active ingredient thereof are also disclosed.

4 Claims, No Drawings

4-SPIROINDOLINE PIPERIDINES PROMOTE RELEASE OF GROWTH HORMONE

This application is a provisional of 60/016,302, filed Mar. 21, 1996.

BACKGROUND OF THE INVENTION

Growth hormone, which is secreted from the pituitary, stimulates growth of all tissues of the body that are capable of growing. In addition, growth hormone is known to have the following basic effects on the metabolic processes of the body: (1) Increased rate of protein synthesis in all cells of the body; (2) Decreased rate of carbohydrate utilization in cells of the body; (3) Increased mobilization of free fatty acids and use of fatty acids for energy. A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recombinant growth hormone has become available which, while no longer carrying any risk of disease transmission, is still a very expensive product which must be given by injection or by a nasal spray. Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. Non peptidal growth hormone secretagogues with a benzolactam structure are disclosed in e.g., U.S. Pat. Nos. 5,206,235, 5,283,241, 5,284,841, 5,310,737 and 5,317,017. Other growth hormone secretagogues are disclosed e.g., in U.S. Pat. Nos. 5,536,716 and 5,578,593, and PCT Patent Publications WO 94/13696, WO 94/19367, and WO 95/09633. The instant compounds are low molecular weight peptide analogs for promoting the release of growth hormone which have good stability in a variety of physiological environments and which may be administered parenterally, nasally or by the oral route.

SUMMARY OF THE INVENTION

The instant invention is directed to 4-spiroindoline piperidine compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food or wool production where the stimulation of growth hormone will result in a larger, more productive animal. Thus, it is an object of the instant invention to describe the heterocyclic spiroindolines compounds. It is a further object of this invention to describe procedures for the preparation of such compounds. A still further object is to describe the use of such compounds to increase the secretion of growth hormone in humans and animals. A still further object of this invention is to describe compositions containing the heterocyclic spiroindoline compounds for the use of treating humans and animals so as to increase the level of growth hormone secretions. Further objects will become apparent from a reading of the following description.

DESCRIPTION OF THE INVENTION

The compounds of the present invention are described by structural Formula I:

Formula I

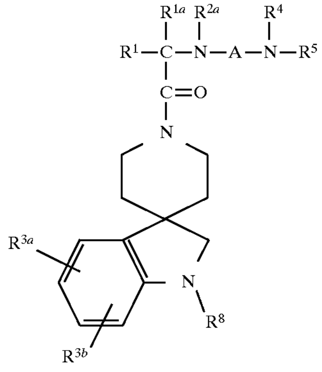

wherein:

$R^1$ is selected from the group consisting of:

$C_1$–$C_{10}$ alkyl, -aryl-, aryl ($C_1$–$C_6$ alkyl)-, heteroaryl-, heteroaryl($C_1$–$C_6$ alkyl)-, ($C_3$–$C_7$ cycloalkyl)-($C_1$–$C_6$ alkyl)-, ($C_1$–$C_5$ alkyl)-K-($C_1$–$C_5$ alkyl)-, aryl-($C_0$–$C_5$ alkyl)-K-($C_1$–$C_5$ alkyl)-, heteroaryl-($C_0$–$C_5$ alkyl)-K-($C_1$–$C_5$ alkyl)-, and ($C_3$–$C_7$ cycloalkyl)-($C_0$–$C_5$ alkyl)-K-($C_1$–$C_5$ alkyl)-, wherein K is —O—, $—S(O)_m—$, $—N(R^2)C(O)—$, $—C(O)N(R^2)—$, —OC(O)—, —C(O)O—, $—CR^2{=}CR^2—$ or —C≡C—, wherein $R^2$ and alkyl may be further substituted with 1 to 9 halo, $—S(O)_mR^{2a}$, 1 to 3 of $—OR^{2a}$, or $—C(O)OR^{2a}$, and wherein aryl is phenyl or naphthyl, and heteroaryl is selected from indolyl, thiophenyl, furanyl, benzothiopheneyl, benzofuranyl, pyridinyl, quinolinyl, triazolyl, imidazolyl, thiazolyl, and benzimidazolyl, wherein aryl and heteroaryl are unsubstituted or substituted with phenyl, phenoxy, halophenyl, 1 to 3 of -$C_1$–$C_6$ alkyl, 1 to 3 of halo, 1 to 2 of $—OR^2$, methylenedioxy, $—S(O)_mR^2$, 1 to 2 of $—CF_3$, $—OCF_3$, nitro, $—N(R^2)(R^2)$, $—N(R^2)C(O)(R^2)$, $—C(O)OR^2$, $—C(O)N(R^2)(R^2)$, $—SO_2N(R^2)(R^2)$, $—N(R^2)SO_2$-aryl, or $—N(R^2)SO_2R^2$;

$R^{1a}$ is hydrogen or $C_1$–$C_4$ alkyl;

$R^2$ is selected from the group consisting of:

hydrogen, -$C_1$–$C_6$ alkyl, -$C_3$–$C_7$ cycloalkyl, and $—CH_2$-phenyl, wherein the alkyl or the cyloalkyl is unsubstituted or substituted with a substituent selected from: hydroxyl, $C_1$–$C_3$ alkoxy, thioalkyl, and $C(O)OR^{2a}$, and wherein if two -$C_1$–$C_6$ alkyl groups are present on one atom, the groups may be optionally joined to form a $C_3$–$C_8$ cyclic ring selected from the group consisting of pyrrolidine, piperidine, piperazine, morpholine, and thiomorpholine;

$R^{2a}$ is hydrogen or $C_1$–$C_6$ alkyl;

$R^{3a}$ and $R^{3b}$ are independently selected from:

hydrogen, phenyl, phenoxy, halophenyl, -$C_1$–$C_6$ alkyl, halo, —$OR^2$, methylenedioxy, —$S(O)_mR^2$, —$CF_3$, —$OCF_3$, nitro, —$N(R^2)(R^2)$, —$N(R^2)C(O)(R^2)$, —$C(O)OR^2$, —$C(O)N(R^2)(R^2)$, —$SO_2N(R^2)(R^2)$, —$N(R^2)SO_2$-aryl, and —$N(R^2)SO_2R^2$;

$R^4$ is independently hydrogen, $C_1$–$C_6$ alkyl or substituted $C_1$–$C_6$ alkyl where the substituents are selected from 1 to 5 halo, 1 to 3 hydroxy, phenyl, and $C_1$–$C_6$ alkoxycarbonyl;

$R^5$ is selected from the definitions of $R^4$ or $R^5$ and $R^4$ may be taken together to form —$(CH_2)_d$—$L_a(CH_2)_e$— where $L_a$ is —$C(R^2)_2$—, —O—, —$S(O)_m$— or —$N(R^2)$—, d and e are independently 1 to 3 and $R^2$ is as defined above;

A is:

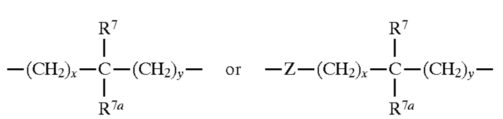

where Z is —$N(R^6)$— or —O—, where $R^{6a}$ is hydrogen or $C_1$–$C_6$ alkyl;

$R^7$ and $R^{7a}$ are independently selected from:

hydrogen, $C_1$–$C_6$ alkyl, trifluoromethyl, phenyl, and substituted $C_1$–$C_6$ alkyl where the substituents are selected from: imidazolyl, naphthyl, phenyl, indolyl, p-hydroxyphenyl, —$OR^2$, —$S(O)_mR^2$, —$C(O)OR^2$, $C_3$–$C_7$ cycloalkyl, —$N(R^2)(R^2)$, —$C(O)N(R^2)(R^2)$, or $R^7$ and $R^{7a}$ may independently be joined to one or both of $R^4$ group to form an alkylene bridge between the terminal nitrogen and the alkyl portion of the $R^7$ or $R^{7a}$ groups, wherein the bridge contains 1 to 5 carbons atoms, or $R^7$ and $R^{7a}$ can be joined to one another to form $C_3$–$C_7$ cycloalkyl;

$R^8$ is selected from the group consisting of:

—$(C{=}NH)$—$N(R^2)(R^2)$, —$(C{=}NR^2)$—$R^2$, —$(C{=}N$—$C{\equiv}N)$—$N(R^2)(R^2)$, —$(C{=}N$—$NO_2)$—$N(R^2)(R^2)$, —$(C{=}N$—$SO_2$—$NH_2)$—$N(R^2)(R^2)$, and heteroaryl, wherein the heteroaryl is optionally substituted with substituents selected from the group consisting of:

hydrogen, phenyl, phenoxy, halophenyl, -$C_1$–$C_6$ alkyl, halo, —$OR^2$, methylenedioxy, —$S(O)_mR^2$, —$CF_3$, —$OCF_3$, nitro, —$N(R^2)(R^2)$, —$N(R^2)C(O)(R^2)$, —$C(O)OR^2$, —$C(O)N(R^2)(R^2)$, —$SO_2N(R^2)(R^2)$, —$N(R^2)SO_2$-aryl, or —$N(R^2)SO_2R^2$ and wherein heteroaryl as used immediately above is intended to include aromatic residues of 5- and 6-membered rings with 1 to 3 heteroatoms or fused 5 and 6 membered bicyclic rings with 1 to 3 heteroatoms of nitrogen, sulfur and oxygen, such as a heteroaryl selected from the group consisting of: pyridine, indole, tetrazole, thiophene, furan, benzothiophene, benzofuran, quinoline, triazole, oxadiazole, thiadiazole, pyrimidine, pyrazine, imidazole, thiazole, dioxathiadiazole and benzimidazole;

m is 0, 1, or 2;

x and y are independently 0, 1, 2 or 3;

and pharmaceutically acceptable salts and individual diastereomers thereof.

In the above structural formula and throughout the instant specification, the following terms have the indicated meanings:

The alkyl groups specified above are intended to include those alkyl groups of the designated length in either a straight or branched configuration and if two carbon atoms or more they may include a double or a triple bond. Exemplary of such alkyl groups are methyl, ethyl, propyl, isopropyl, butyl, sec-butyl, tertiary butyl, pentyl, isopentyl, hexyl, isohexyl, allyl, propargyl, and the like.

The alkoxy groups specified above are intended to include those alkoxy groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

The term "halogen" is intended to include the halogen atom fluorine, chlorine, bromine and iodine.

The term "aryl" within the present invention, unless otherwise specified, is intended to include aromatic rings, such as carbocyclic and heterocyclic aromatic rings including: phenyl, naphthyl, thiazolyl, thiadiazolyl, pyridyl, 1-H-tetrazol-5-yl, isothiazolyl, oxazolyl, isoxazolyl, thienyl, oxadiazolyl, benzothienyl, benzofuranyl, benzimidazolyl, imidazolyl, indolyl, thiopheneyl, pyrimidinyl, pyrazolyl, pyrrazinyl, quinolinyl, and isoquinolinyl, which are unsubstituted or substituted with 1 to 3 of $C_1$–$C_6$ alkyl, 1 to 3 of halogen, 1 to 2 of —$OR^2$, methylenedioxy, —$S(O)_mR^2$, 1 to 2 of —$CF_3$, —$OCF_3$, nitro, —$N(R^2)C(O)(R^2)$, —$C(O)OR^2$, —$C(O)N(R^2)(R^2)$, -1H-tetrazol-5-yl, —$SO_2N(R^2)(R^2)$, —$N(R^2)SO_2$ phenyl, or —$N(R^2)SO_2R^2$, wherein $R^2$ is as defined herein.

Certain of the above defined terms (such as "$R^2$") may occur more than once within the above formula and upon such occurrence each term shall be defined independently of the other.

Preferred compounds of the instant invention include those of Formula Ia:

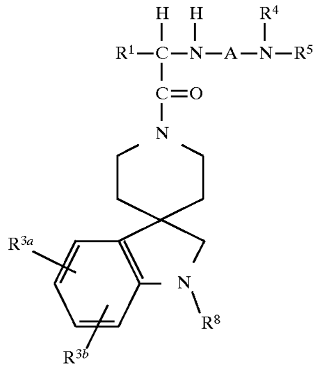

Formula Ia wherein:

$R^1$ is selected from the group consisting of:

$C_1$–$C_{10}$ alkyl, -aryl-, aryl ($C_1$–$C_6$ alkyl)-, heteroaryl-, heteroaryl($C_1$–$C_6$ alkyl)-, ($C_3$–$C_7$ cycloalkyl)-($C_1$–$C_6$ alkyl)-, ($C_1$–$C_5$ alkyl)-K-($C_1$–$C_5$ alkyl)-, aryl-($C_0$–$C_5$ alkyl)-K-($C_1$–$_5$ alkyl)-, heteroaryl-($C_0$–$C_5$ alkyl)-K-($C_1$–$C_5$ alkyl)-, and ($C_3$–$C_7$ cycloalkyl)-($C_0$–$C_5$ alkyl)-K-($C_1$–$C_5$ alkyl)-, wherein K is —O—, —$S(O)_m$—, —$N(R^2)C(O)$—, —$C(O)N(R^2)$—, —OC(O)—, —C(O)O—, —$CR^2$=$CR^2$— or —C≡C—, wherein $R^2$ and alkyl may be further substituted with 1 to 9 halo, —$S(O)_mR^{2a}$, 1 to 3 of —$OR^{2a}$, or —$C(O)OR^{2a}$, and wherein aryl is phenyl or naphthyl, and heteroaryl is selected from indolyl, azaindolyl, thiophenyl, furanyl, benzothiopheneyl, benzofuranyl, pyridinyl, quinolinyl, triazolyl, imidazolyl, thiazolyl, and benzimidazolyl, wherein aryl and heteroaryl are unsubstituted or substituted with phenyl, phenoxy, halophenyl, 1 to 3 of -$C_1$–$C_6$ alkyl, 1 to 3 of halo, 1 to 2 of —$OR^2$, methylenedioxy, —$S(O)_mR^2$, 1 to 2 of —$CF_3$, —$OCF_3$, nitro, —$N(R^2)(R^2)$, —$N(R^2)C(O)(R^2)$, —$C(O)OR^2$, —$C(O)N(R^2)(R^2)$, —$SO_2N(R^2)(R^2)$, —$N(R^2)SO_2$-aryl, or —$N(R^2)SO_2R^2$;

$R^2$ is selected from the group consisting of: hydrogen, -$C_1$–$C_6$ alkyl, -$C_3$–$C_7$ cycloalkyl, and —$CH_2$-phenyl, wherein the alkyl or the cyloalkyl is unsubstituted or substituted with a substituent selected from: hydroxyl, $C_1$–$C_3$ alkoxy, thioalkyl, and $C(O)OR^{2a}$, and wherein if two -$C_1$–$C_6$ alkyl groups are present on one atom, the groups may be optionally joined to form a $C_3$–$C_8$ cyclic ring selected from the group consisting of pyrrolidine, piperidine, piperazine, morpholine, and thiomorpholine;

$R^{3a}$ and $R^{3b}$ are independently selected from:

hydrogen, phenyl, phenoxy, halophenyl, -$C_1$–$C_6$ alkyl, halo, —$OR^2$, methylenedioxy, —$S(O)_mR^2$, —$CF_3$, —$OCF_3$, nitro, —$N(R^2)(R^2)$, —$N(R^2)C(O)(R^2)$, —$C(O)OR^2$, —$C(O)N(R^2)(R^2)$, —$SO_2N(R^2)(R^2)$, —$N(R^2)SO_2$-aryl, and —$N(R^2)SO_2R^2$;

$R^4$ is independently hydrogen, $C_1$–$C_6$ alkyl or substituted $C_1$–$C_6$ alkyl where the substituents are selected from 1 to 5 halo, 1 to 3 hydroxy, phenyl, and $C_1$–$C_6$ alkoxy-carbonyl;

$R^5$ is selected from the definitions of $R^4$ or $R^5$ and $R^4$ may be taken together to form —$(CH_2)_d$—$L_a(CH_2)_e$— where $L_a$ is —$C(R^2)_2$—, —O—, —$S(O)_m$— or —$N(R^2)$—, d and e are independently 1 to 3 and $R^2$ is as defined above;

A is:

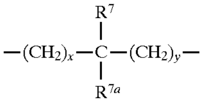

or

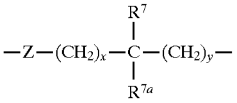

where Z is —$N(R^{6a})$— or —O—, where $R^{6a}$ is hydrogen or $C_1$–$C_6$ alkyl;

$R^7$ and $R^{7a}$ are independently selected from:

hydrogen, $C_1$–$C_6$ alkyl, trifluoromethyl, phenyl, and substituted $C_1$–$C_6$ alkyl where the substituents are selected from: imidazolyl, naphthyl, phenyl, indolyl, p-hydroxyphenyl, —$OR^2$, —$S(O)_mR^2$, —$C(O)OR^2$, $C_3$–$C_7$ cycloalkyl, —$N(R^2)(R^2)$, —$C(O)N(R^2)(R^2)$, or $R^7$ and $R^{7a}$ may independently be joined to one or both of $R^4$ group to form an alkylene bridge between the terminal nitrogen and the alkyl portion of the $R^7$ or $R^{7a}$ groups, wherein the bridge contains 1 to 5 carbons atoms, or $R^7$ and $R^{7a}$ can be joined to one another to form $C_3$–$C_7$ cycloalkyl;

$R^8$ is selected from the group consisting of:

—(C=NH)—$N(R^2)(R^2)$, —(C=$NR^2$)—$R^2$, —(C=N—C≡N)—$N(R^2)(R^2)$, —(C=N—$NO_2$)—$N(R^2)(R^2)$, —(C=N—$SO_2$—$NH_2$)—$N(R^2)(R^2)$, and heteroaryl, wherein the heteroaryl is optionally substituted with substituents selected from the group consisting of:

hydrogen, phenyl, phenoxy, halophenyl, -$C_1$–$C_6$ alkyl, halo, —$OR^2$, methylenedioxy, —$S(O)_mR^2$, —$CF_3$, —$OCF_3$, nitro, —$N(R^2)(R^2)$, —$N(R^2)C(O)(R^2)$, —$C(O)OR^2$, —$C(O)N(R^2)(R^2)$, —$SO_2N(R^2)(R^2)$, —$N(R^2)SO_2$-aryl, or —$N(R^2)SO_2R^2$ and wherein heteroaryl as used immediately above is intended to include aromatic residues of 5- and 6-membered rings with 1 to 3 heteroatoms or fused 5 and 6 membered bicyclic rings with 1 to 3 heteroatoms of nitrogen, sulfur and oxygen, such as a heteroaryl selected from the group consisting of: pyridine, triazole, thiophene, furan, thiophene, oxadiazole, thiadiazole, tetrazole, imidazole, thiazole, dioxathiadiazole, purimidine and pyrazine;

m is 0, 1, or 2;

x and y are independently 0, 1, 2 or 3;

and pharmaceutically acceptable salts and individual diastereomers thereof.

More preferred compounds of the instant invention include those of Formula Ib:

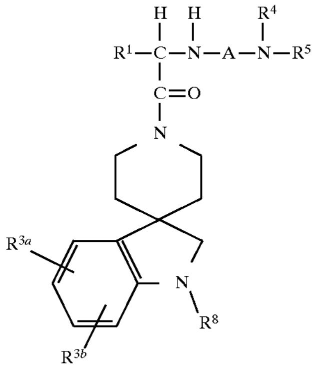

Formula Ib wherein:

$R^1$ is selected from the group consisting of:

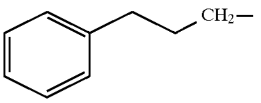

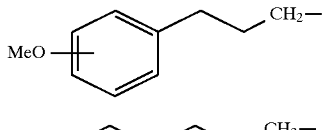

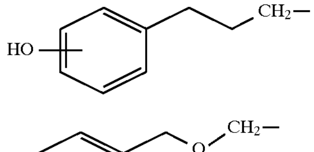

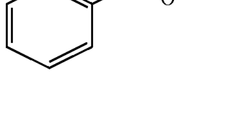

-continued

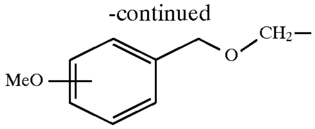

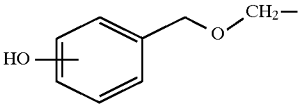

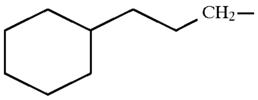

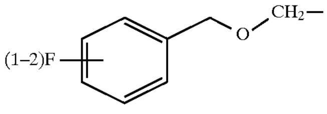

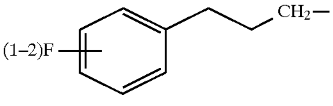

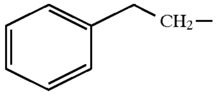

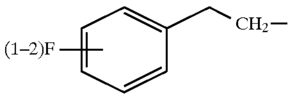

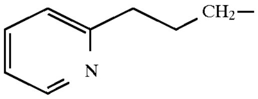

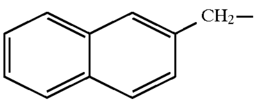

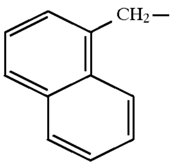

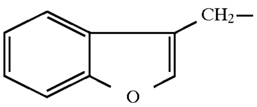

$R^2$ is selected from the group consisting of:

hydrogen, $-C_1-C_6$ alkyl, $-C_3-C_7$ cycloalkyl, and $—CH_2$-phenyl, wherein the alkyl or the cyloalkyl is unsubstituted or substituted with a substituent selected from: hydroxyl, $C_1-C_3$ alkoxy, thioalkyl, and $C(O)OR^{2a}$, and wherein if two $-C_1-C_6$ alkyl groups are present on one atom, the groups may be optionally joined to form a $C_3-C_8$ cyclic ring selected from the group consisting of pyrrolidine, piperidine, piperazine, morpholine, and thiomorpholine;

$R^{3a}$ and $R^{3b}$ are independently selected from:

hydrogen, $-C_1-C_6$ alkyl, halo, and $—OR^2$;

$R^4$ is independently hydrogen, $C_1-C_6$ alkyl or substituted $C_1-C_6$ alkyl where the substituents are selected from 1 to 5 halo, 1 to 3 hydroxy, phenyl, and $C_1-C_6$ alkoxycarbonyl;

$R^5$ is selected from the definitions of $R^4$ or $R^5$ and $R^4$ may be taken together to form $—(CH_2)_d—L_a(CH_2)_e—$ where $L_a$ is $—C(R^2)_2—$, $—O—$, $—S(O)_m—$ or $—N(R^2)—$, d and e are independently 1 to 3 and $R^2$ is as defined above;

A is:

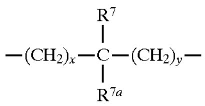 or 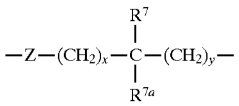

where Z is $—N(R^6)—$ or $—O—$, where $R^6$ is hydrogen or $C_1-C_6$ alkyl;

$R^7$ and $R^{7a}$ are independently selected from:

hydrogen, $C_1-C_6$ alkyl, trifluoromethyl, phenyl, and substituted $C_1-C_6$ alkyl where the substituents are selected from: imidazolyl, naphthyl, phenyl, indolyl, p-hydroxyphenyl, $—OR^2$, $—S(O)_mR^2$, $—C(O)OR^2$, $C_3-C_7$ cycloalkyl, $—N(R^2)(R^2)$, $—C(O)N(R^2)(R^2)$, or $R^7$ and $R^{7a}$ may independently be joined to one or both of $R^4$ group to form an alkylene bridge between the terminal nitrogen and the alkyl portion of the $R^7$ or $R^{7a}$ groups, wherein the bridge contains 1 to 5 carbons atoms, or $R^7$ and $R^{7a}$ can be joined to one another to form $C_3-C_7$ cycloalkyl;

$R^8$ is selected from the group consisting of:

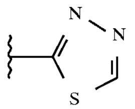

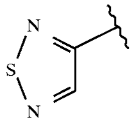

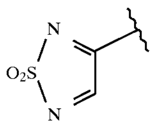

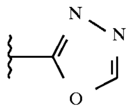

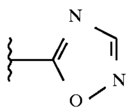

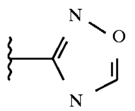

-continued

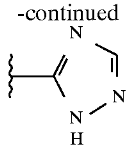

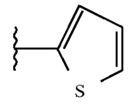

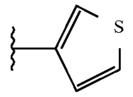

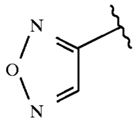

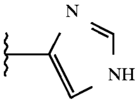

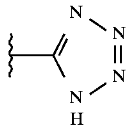

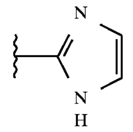

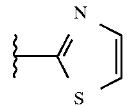

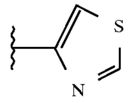

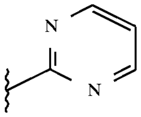

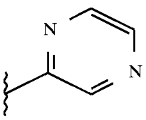

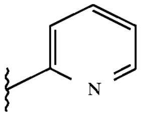

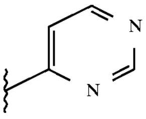

or their regioisomers, and —(C═N—C≡N)—NH—$CH_3$, —(C═N—C≡N)—NH—$CH_2CH_3$, and —(C═N—C≡N)—NH-phenyl, wherein the heteroaryl is optionally substituted with substituents selected from the group consisting of: hydrogen, -$C_1$–$C_6$ alkyl, halo, —$OR^2$,—$CF_3$, nitro, and —$N(R^2)(R^2)$;

m is 0, 1, or 2;

x and y are independently 0, 1, 2 or 3;

and pharmaceutically acceptable salts and individual diastereomers thereof.

Specific compounds within the scope of the instant invention include:

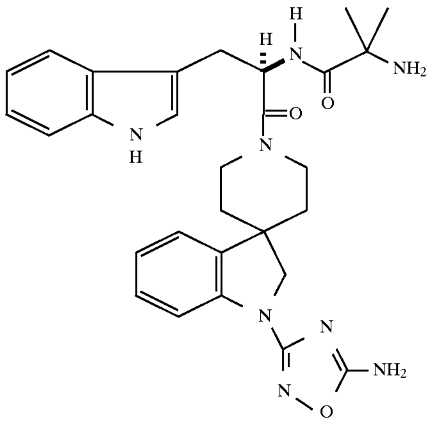

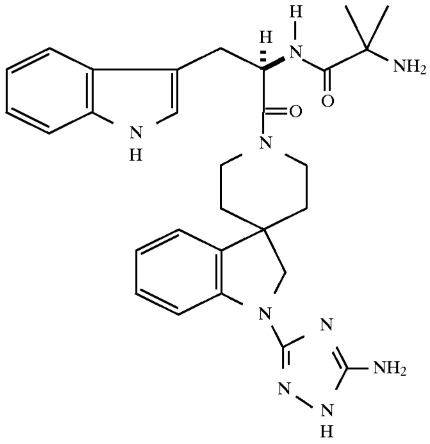

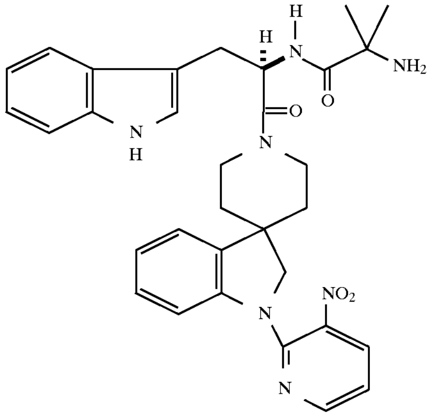

-continued
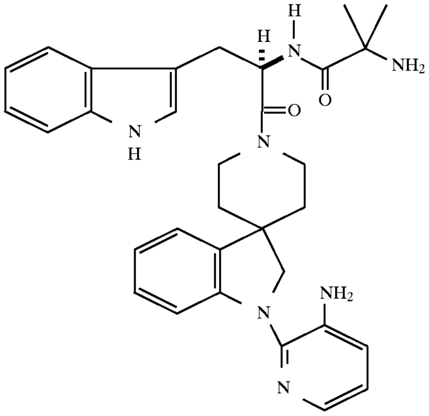
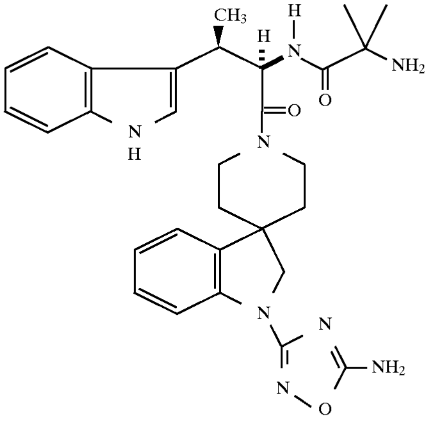
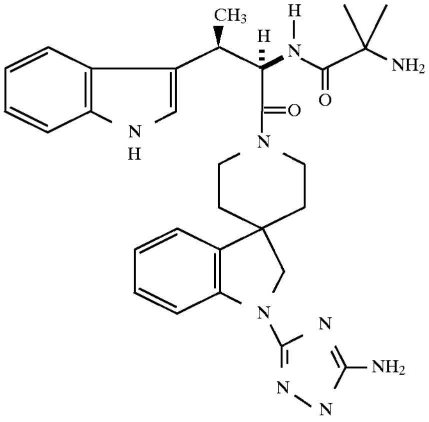
-continued
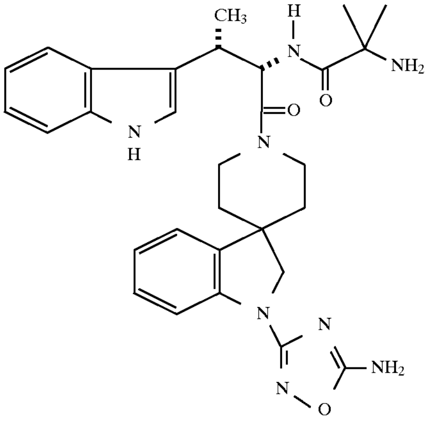
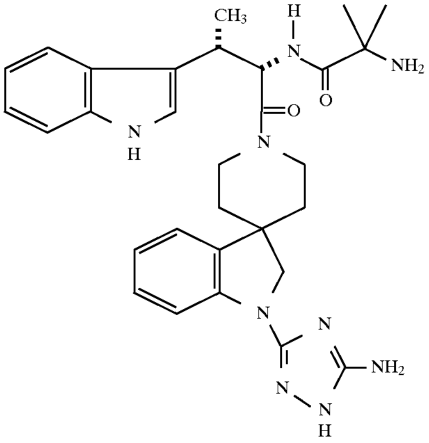
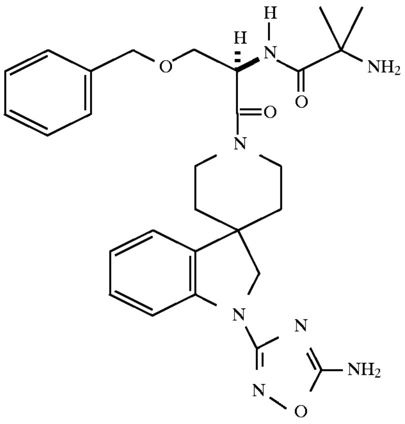

-continued
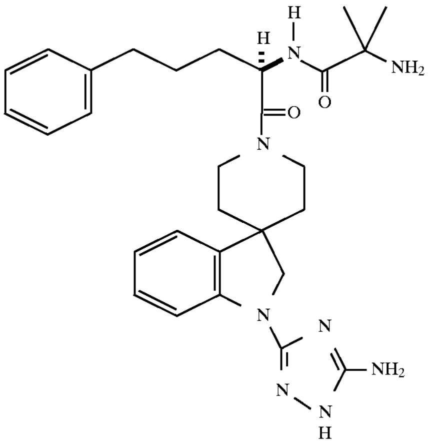
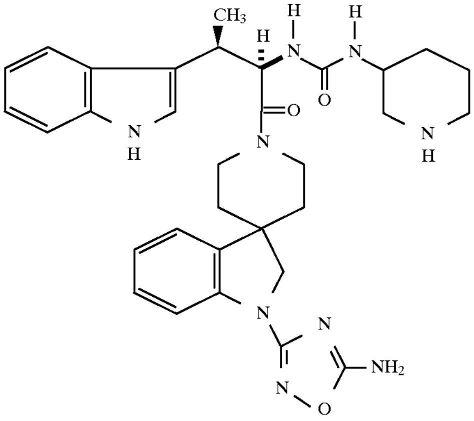
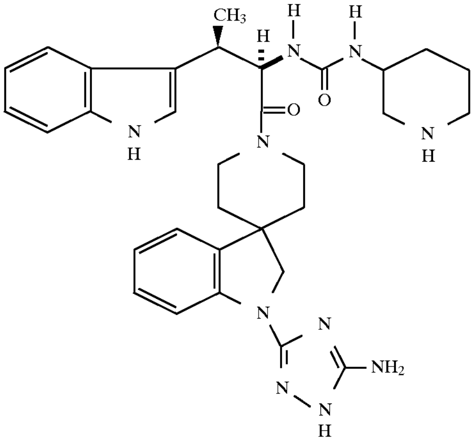
-continued
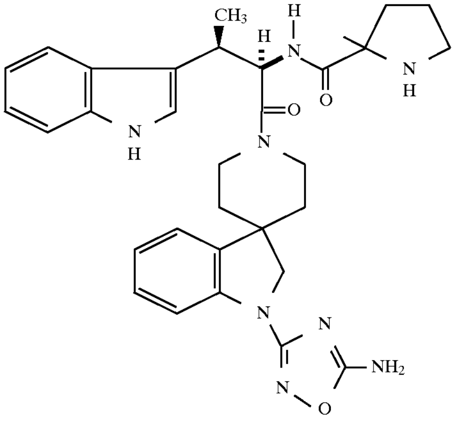
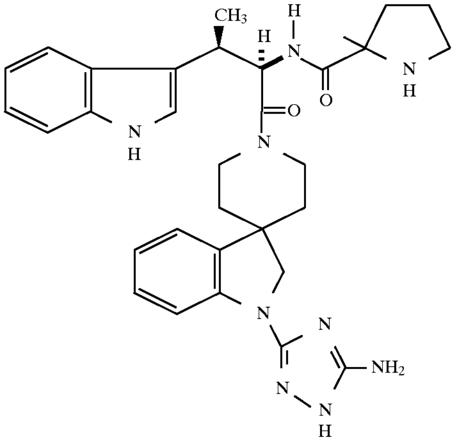
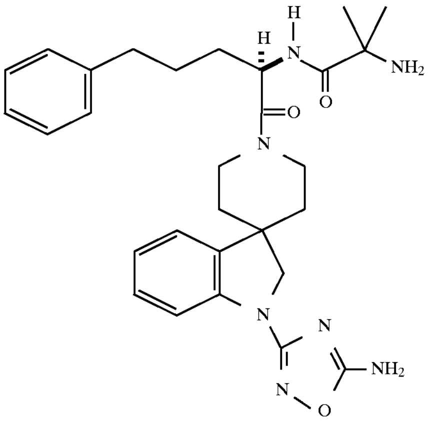

-continued

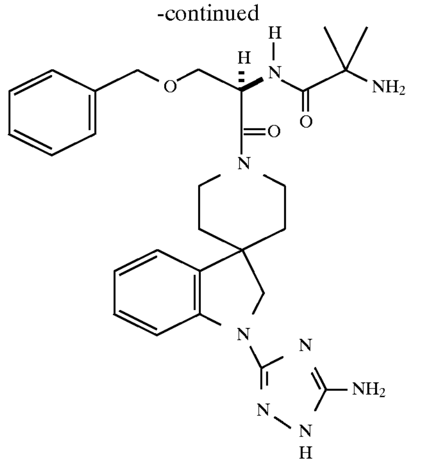

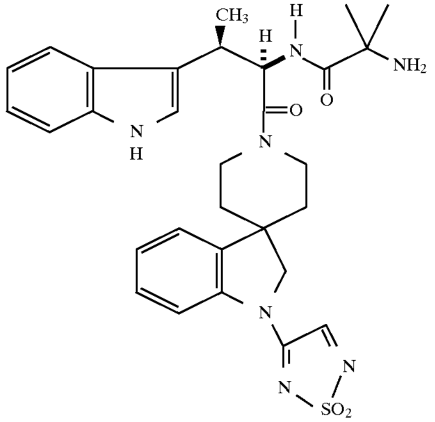

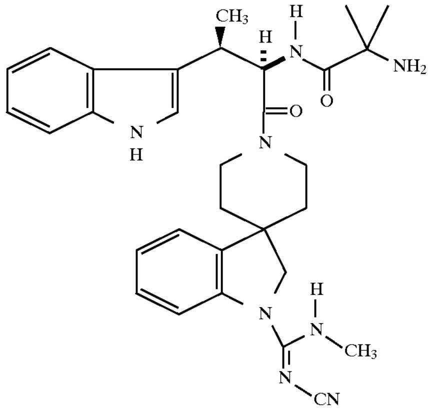

and pharmaceutically acceptable salts and individual diastereomers thereof.

Throughout the instant application, the following abbreviations are used with the following meanings:

Bu butyl

Bn benzyl

BOC, Boc t-butyloxycarbonyl

BOP Benzotriazol-1-yloxy tris/dimethylamino)-phosphonium hexafluorophosphate calc. calculated CBZ, Cbz Benzyloxycarbonyl DCC Dicyclohexylcarbodiimide DMF N,N-dimethylformamide DMAP 4-Dimethylaminopyridine EDC 1-(3-dimethylaminopropyl)-3-ethylcarbodi-imide hydrochloride EI-MS Electron ion-mass spectroscopy Et ethyl eq. equivalent(s)

FAB-MS Fast atom bombardment-mass spectroscopy

HOBT, HOBt Hydroxybenztriazole

HPLC High pressure liquid chromatography

KHMDS Potassium bis(trimethylsilyl)amide

LAH Lithium aluminum hydride

LHMDS Lithium bis(trimethylsilyl)amide

Me methyl

MF Molecular formula

MHz Megahertz

MPLC Medium pressure liquid chromatography

NMM N-Methylmorpholine

NMR Nuclear Magnetic Resonance

Ph phenyl

Pr propyl prep. prepared

TFA Trifluoroacetic acid

THF Tetrahydrofuran

TLC Thin layer chromatography

TMS Tetramethylsilane

The compounds of the instant invention all have at least one asymmetric center. Additional asymmetric centers may be present depending upon the nature of the various substituents on the molecule. Each such asymmetric center will independently produce two optical isomers and it is intended that all of the possible optical isomers and diastereomers in mixture and as pure or partially purified compounds are included within the scope of the present invention.

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The preparation of compounds of Formula I of the present invention (illustrated with $R^{1a}$ and $R^{2a}$ as hydrogen for clarity) may be carried out in sequential or convergent synthetic routes. Syntheses detailing the preparation of the compounds of Formula I in a sequential manner are presented in the following reaction schemes.

The phrase "standard peptide coupling reaction conditions" is used repeatedly here, and it means coupling a carboxylic acid with an amine using an acid activating agent such as EDC, DCC, and BOP in a inert solvent such as dichloromethane in the presence of a catalyst such as HOBT. The uses of protective groups for amine and carboxylic acid to facilitate the desired reaction and minimize undesired reactions are well documented. Conditions required to remove protecting groups which may be present and can be found in Greene, T, and Wuts, P. G. M., *Protective Groups in Organic Synthesis*, John Wiley & Sons, Inc., New York, N.Y. 1991. CBZ and BOC were used extensively in the synthesis, and their removal conditions are known to those skilled in the art. For example, removal of CBZ groups can be achieved by a number of methods known in the art; for example, catalytic hydrogenation with hydrogen in the presence of a noble metal or its oxide such as palladium on activated carbon in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethylsulfide. Removal of BOC protecting groups is carried out in a solvent such as methylene chloride or methanol or ethyl acetate, with a strong acid, such as trifluoroacetic acid or hydrochloric acid or hydrogen chloride gas.

The protected amino acid derivatives 1 are, in many cases, commercially available, where the protecting group L is, for example, BOC or CBZ groups. Other protected amino acid derivatives 1 can be prepared by literature methods (Williams, R. M. *Synthesis of Optically Active α-Amino Acids*, Pergamon Press: Oxford, 1989). Many of the piperidines and pyrrolidines of Formula 2 are either commercially available or known in the literature and others can be prepared following literature methods described for analogous compounds. Some of these methods are illustrated in the subsequent schemes. The skills required in carrying out the reaction and purification of the resulting reaction products are known to those in the art. Purification procedures includes crystallization, normal phase or reverse phase chromatography.

SCHEME 1

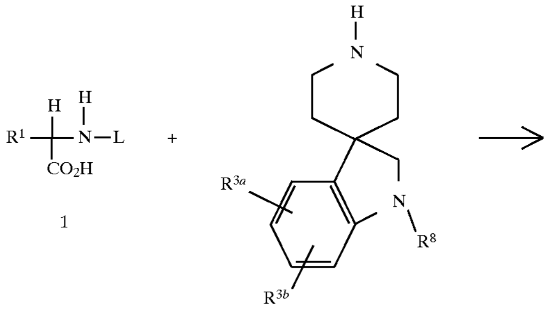

-continued

SCHEME 1

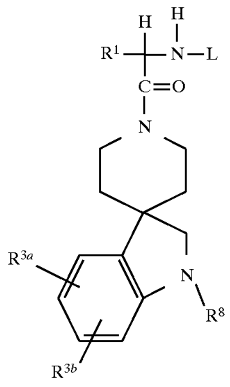

3

Intermediates of Formula 3 may be synthesized as described in Scheme 1. Coupling of amine of Formula 2, whose preparations are described later if they are not commercially available, to protected amino acids of Formula 1, wherein L is a suitable protecting group, is conveniently carried out under standard peptide coupling conditions.

SCHEME 2

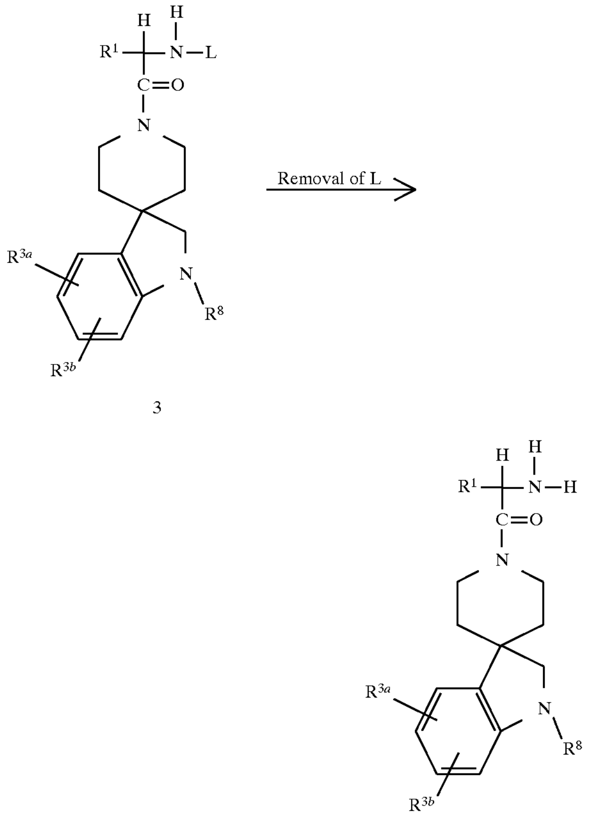

3

3

Conversion of 3 to intermediate 4 can be carried out as illustrated in Scheme 2 by removal of the protecting group L (CBZ, BOC, etc.)

SCHEME 3

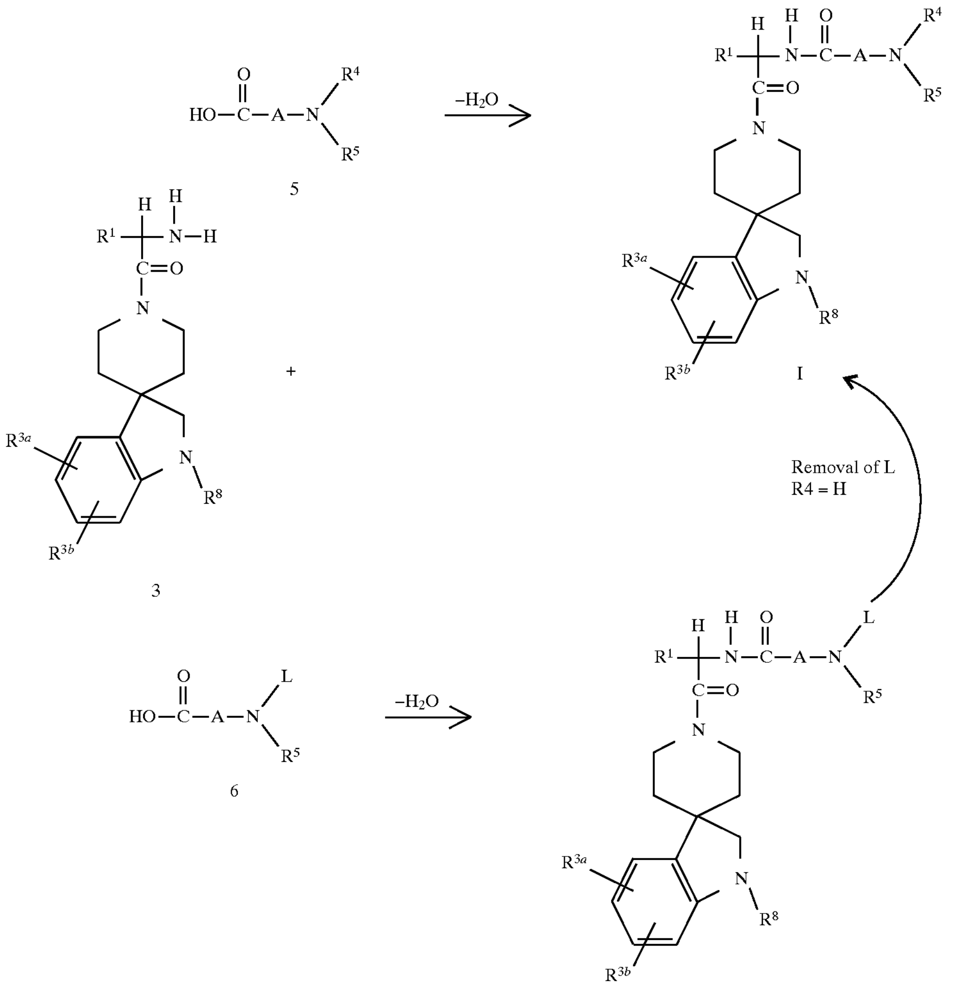

5 3 6 7 I

Intermediates of Formula 5, wherein A is $—(CH_2)_x—C(R^7)(R^{7a})—(CH_2)_y—$ may be prepared as shown in Scheme 3 by coupling intermediates of Formula 4 to amino acids of Formula 5 under the standard peptide coupling reaction conditions. The amino acids 5, as amino acid 1, are either commercially available or can be synthesized by routine methods. Also if $R^4$ or $R^5$ is a hydrogen then the protected amino acids 6 are employed in the coupling reaction, wherein L is a protecting group as defined above. The removal of L in 7 to afford I, where $R^4$=H, can be carried out as noted above.

SCHEME 4

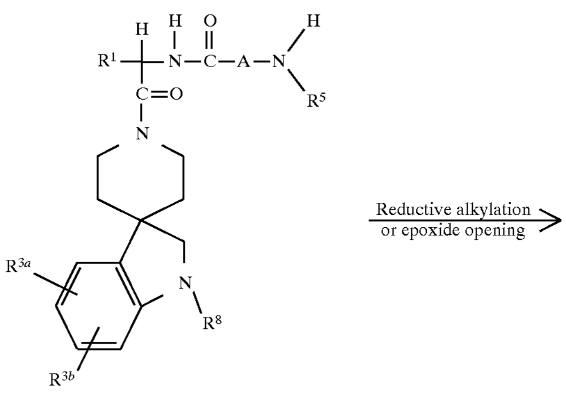

I

-continued

SCHEME 4

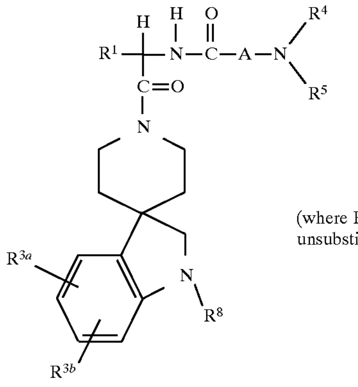

(where $R^4$ is substituted/unsubstituted alkyl)

I

Compounds of Formula I wherein $R^4$ and/or $R^5$ is a hydrogen may be further elaborated to new Compounds I (with most preferred side chains $R^4$=$CH_2$—CH(OH)—$CH_2X$, wherein X=H or OH) which are substituted on the amino group as depicted in Scheme 4. Reductive alkylation of I with an aldehyde is carried out under conditions known in the art; for example, by catalytic hydrogenation with hydrogen in the presence of platinum, palladium, or nickel catalysts or with chemical reducing agents such as sodium cyanoborohydride in a protic solvent such as methanol or ethanol in the present of catalytic amount of acid. Alternatively, a similar transformation can be accomplished via an epoxide opening reaction.

SCHEME 5

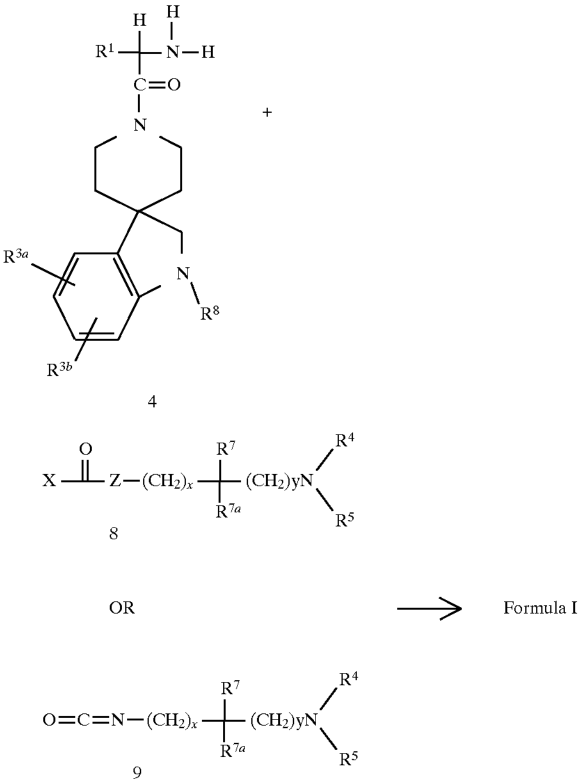

4 + 8 OR 9 Formula I

Compounds of Formula I, wherein A is Z—$(CH_2)_x$—$C(R^7)(R^{7a})$—$(CH_2)_y$ and Z is N—$R^6$ or O may be prepared as shown in Scheme 5 by reacting 4 with reagents 8, wherein X is a good leaving group such as Cl, Br, I, or imidazole. Alternatively, 4 may be reacted with an isocyanate of Formula 9 in an inert solvent such as 1,2-dichloroethane to provide compounds of Formula I where Z is NH.

SCHEME 6

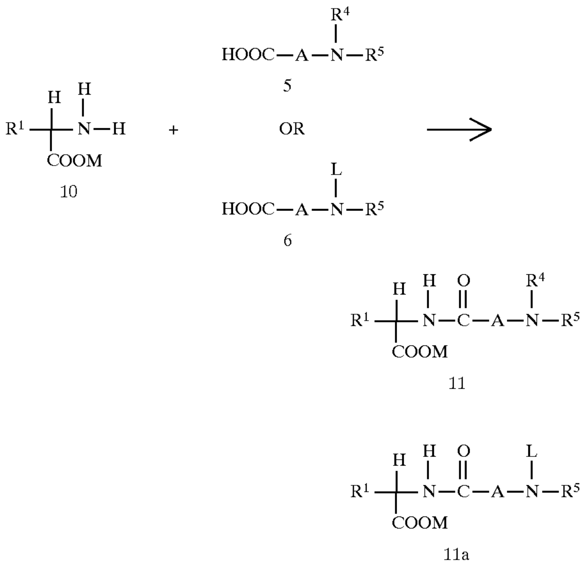

10 + 5 OR 6

11

11a

The compounds of general Formula I of the present invention may also be prepared in a convergent manner as described in reaction Schemes 6, 7 and 8.

The carboxylic acid protected amino acid derivatives 10 are, in many cases, commercially available where M=methyl, ethyl, or benzyl esters. Other ester protected amino acids can be prepared by classical methods familiar to those skilled in the art. Some of these methods include the reaction of the amino acid with an alcohol in the presence of an acid such as hydrochloric acid or p-toluenesulfonic acid and azeotropic removal of water. Other reactions includes the reaction of a protected amino acid with a diazoalkane, or with an alcohol and an acid activating agent such as EDC, DCC in the presence of a catalyst such as DMAP and removal of the protecting group L.

Intermediates of Formula 11 or 11a, may be prepared as shown in Scheme 6 by coupling of amino acid ester 10 to amino acids of Formula 6 or 7. When a urea or carbamate linkage is present in 11 or 11a, it can be introduced as illustrated in Scheme 5.

SCHEME 7

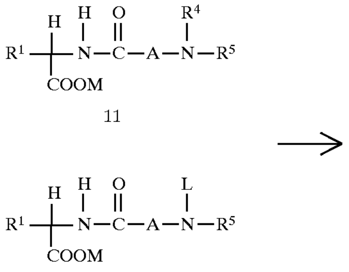

11

11a

-continued

SCHEME 7

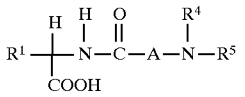

12

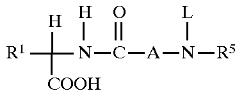

12a

Conversion of the ester 11 or 11a to intermediate acids 12 or 12a may be achieved by a number of methods known in the art as described in Scheme 7. For example, methyl and ethyl esters can be hydrolyzed with lithium hydroxide in a protic solvent like aqueous methanol. In addition, removal of benzyl group can be accomplished by a number of reductive methods including hydrogenation in the presence of palladium catalyst in a protic solvent such as methanol. An allyl ester can be cleaved with tetrakis-triphenylphosphine palladium catalyst in the presence of 2-ethylhexanoic acid in a variety of solvents including ethyl acetate and dichloromethane (see *J. Org. Chem.*, 42, 587 (1982)).

SCHEME 8

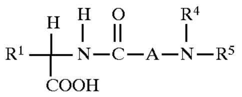

12

+

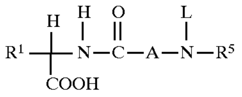

12a

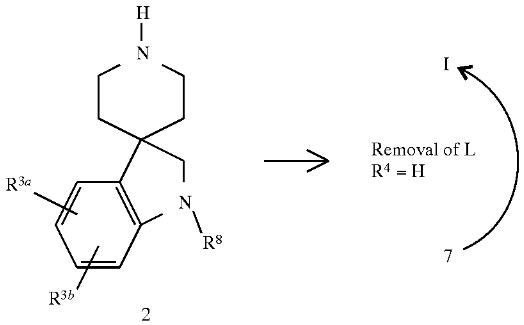

2

7

I

As shown in Scheme 8, acids of formulas 12 and 12a, wherein L is a protecting group, may be coupled to piperidines of formula 2 under standard peptide-type coupling conditions to give compounds of formula 7. Removal of the protecting group L gives compounds of formula I.

SCHEME 9

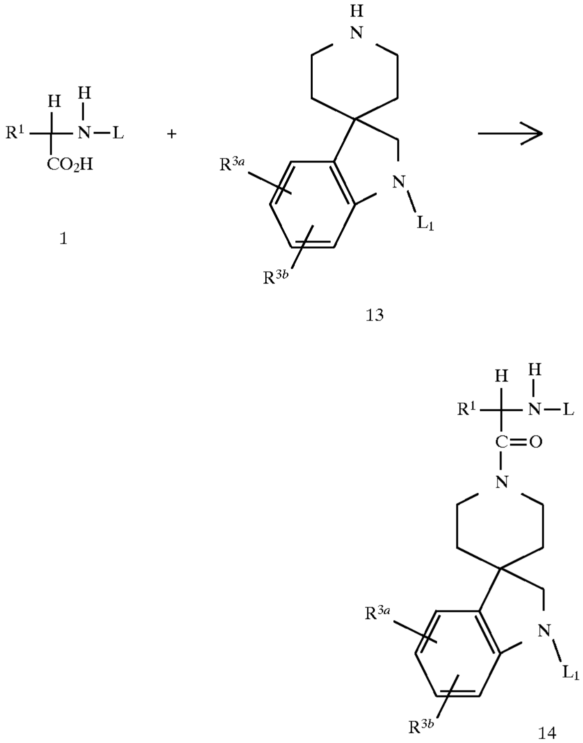

1

13

14

A third approach towards synthesis of compounds of Formula I as shown in Scheme 9 involves coupling of amines of Formula 13, wherein $L_1$ is a suitable protecting group, to amino acids of Formula 1 and is conveniently carried out under standard peptide coupling conditions. The preparation of amines of Formula 13 is described later if such compounds are not commercially available.

SCHEME 10

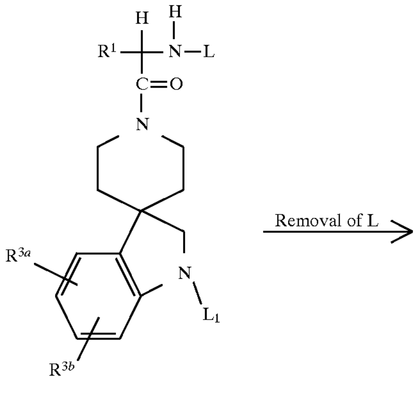

14

-continued

SCHEME 10

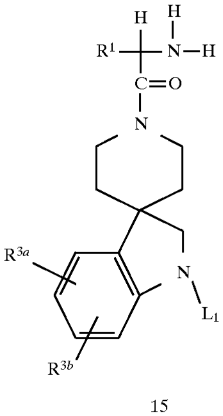

15

Conversion of 14 to intermediate 15 can be carried out as illustrated in Scheme 10 by removal of the protecting group L (CBZ, BOC, etc.). The choice of the protecting group L1 is important because selective removal of L has to be carried out in the presence of $L_1$. These protecting groups and methods of selective removal are well documented in the literature and will be familiar to those skilled in the art.

Intermediates of formulas 16 and 17, wherein A is $-(CH_2)_x-$ $C(R^7)(R^{7a})-(CH_2)_y-$ may be prepared as shown in Scheme 11 by coupling intermediates of Formula 15 to amino acids of Formula 5 under the standard peptide coupling reaction conditions. The amino acids 5, as amino acid 1, are either commercially available or can be synthesized by routine methods. Also if $R^4$ or $R^5$ is a hydrogen then the protected amino acids 6 are employed in the coupling reaction, wherein L is a protecting group as defined above.

SCHEME 12

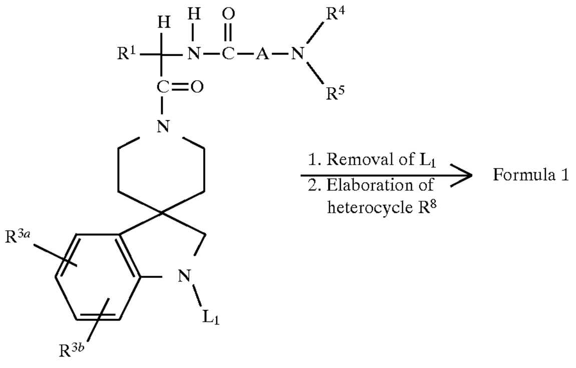

17

SCHEME 11

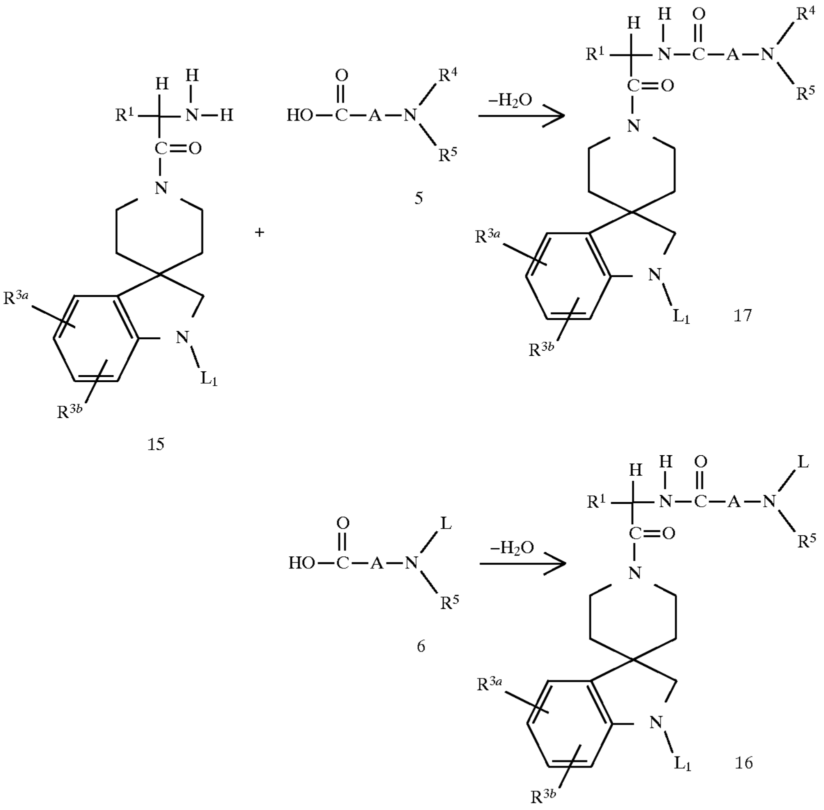

15 5 17 6 16

-continued

SCHEME 12

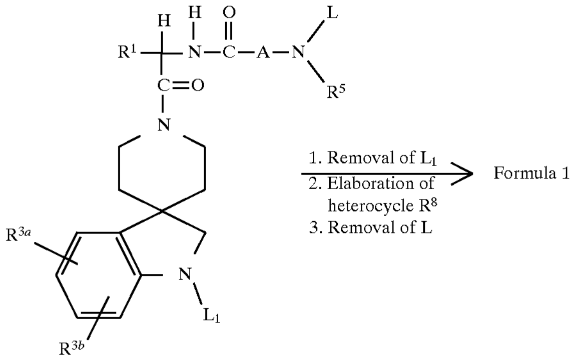

16

As depicted in Scheme 12 the protecting group $L_1$ from the spiroindoline can be removed and the heterocycle $R^8$ can be elaborated by methods that will be described later. Removal of the protecting group L from the amino acid by using chemistry described above provides compounds of Formula 1.

The spiro piperidines of formula 2 may be prepared by a number of methods, including the syntheses as described below.

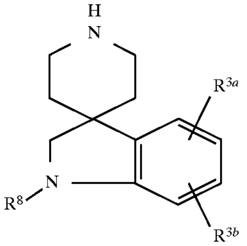

2

The spiropiperidines of formula 2 may be synthesized by methods that are known in the literature (for example H. Ong et al., *J. Med. Chem.*, 1983, 23, 981–986).

SCHEME 13

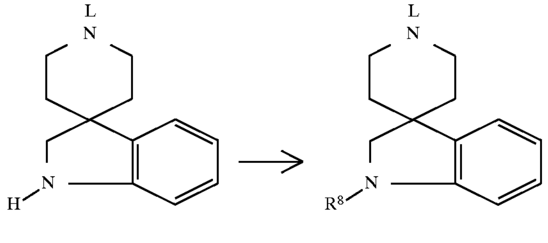

17 18

As shown in Scheme 13 the indoline nitrogen of 17, wherein L is a protecting group such as methyl or benzyl, can be reacted by with a variety of heterocyclic electrophiles to yield spiro piperidines of formula 18, wherein $R^8$ may be a heteroaryl group as described within the scope of the present invention. Compound 17 may be reacted with, for example, with halogenated heterocycles in the presence of base is a suitable solvent like DMSO or DMF to give piperidines of Formula 18. Indeed, the reaction of piperidines related to 17 with o-fluoropyridine to give spiroindoline of formula 18, wherein $R^8$ is an o-pyridyl group, was carried out by Ong et al., and is documented in *J. Med. Chem.*, 1983, 23, 981–986.

SCHEME 14

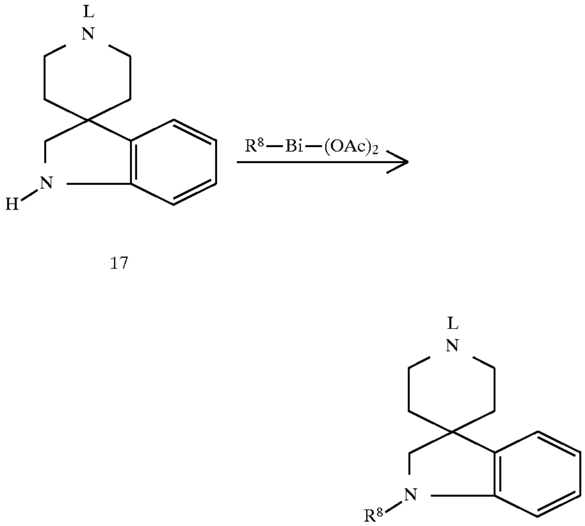

17

18

Other methods that may be employed to prepare heterocyclic spiroindolines include the copper catalyzed N-arylation of amines by triarylbismuth diacetates (D. H. R. Barton et al., *Tetrahedron Lett.*, 1986, 27, 3615 as shown in Scheme 14.

SCHEME 15

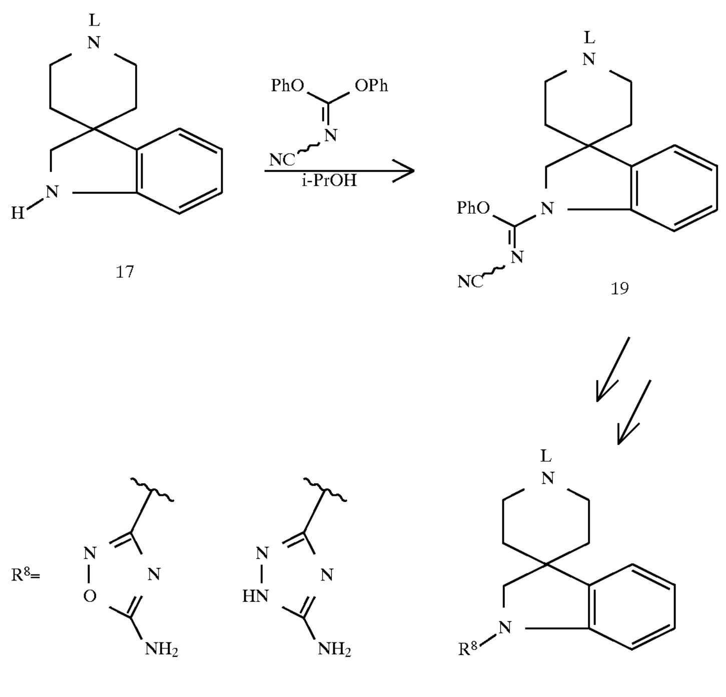

17 19 18

Other methods to convert 17 to 18, wherein $R^8$ is specifically amino-oxadiazole or amino-triazole may be carried out as shown in Scheme 15. Reaction of the indoline 17 with N-cyanodiphen-oxyimidocarbonate can be carried out in a polar solvent like iso-propanol to give the intermediate of Formula 19. Elaboration of 19 to 18, wherein $R^8$ is an amino-oxadiazole or amino-triazole can be accomplished by treatment with hydroxylamine or hydrazine. Likewise, the preparation of cyanoguanidines may be accomplished by treatment with an appropriate amine. Similar functionality at $R^8$ may be introduced by methodology known in the art. The protecting group L can be removed under standard conditions and converted to compounds of Formula 1 by using chem is try described in Schemes 1–8.

The spiro piperidine intermediate 18 (L=Me or Bn), wherein $R^8$ is a heteroaryl as described within the scope of the present invention, can be demethylated or debenzylated to produce 2. For compounds of formula 18, wherein L=Me or Bn, dealkylation can be carried out by a number methods familiar those skilled in the art. For example, dealkylation of 18 be accomplished by reacting it with cyanogen bromide and potassium carbonate in an inert solvent solvent such as dichloromethane to yield a cyanamide which can reduced to give 2 by treatment with lithium aluminum hydride in refluxing tetrahydrofuran, refluxing strong acid like aqueous hydrochloric acid, or with Grignard reagents like methyl magnesium bromide. Alternatively, dealkylation of 18 can be effected with the ACE-Cl method as described in R. Olofson et al., *J. Org. Chem.* 1984, 49, 2795 and references therein. For intermediates of formula 18, wherein L=Bn, removal of benzyl group can be accomplished by reductive methods including hydrogenation in the presence of platinum or palladium catalyst in a protic solvent like methanol.

The compounds of the present invention may also be prepared from a variety of substituted natural and unnatural amino acids of formulas 20. The preparation of many of these acids is described in U.S. Pat. No. 5,206,237. The preparation of these intermediates in racemic form is accomplished by classical methods familiar to those skilled in the art (Williams, R. M. "*Synthesis of Optically Active α-Amino Acids*" Pergamon Press: Oxford, 1989; Vol. 7) Several methods exist to resolve (DL)-

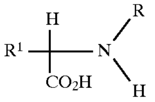

20 amino acids. One of the common methods is to resolve amino or carboxyl protected intermediates by crystallization of salts derived from optically active acids or amines. Alternatively, the amino group of carboxyl protected intermediates may be coupled to optically active acids by using chem is try described earlier. Separation of the individual diastereomers either by chromatographic techniques or by crystallization followed by hydrolysis of the chiral amide furnishes resolved amino acids. Similarly, amino protected intermediates may be converted to a mixture of chiral diastereomeric esters and amides. Separation of the mixture using methods described above and hydrolysis of the individual diastereomers provides (D) and (L) amino acids. Finally, an enzymatic method to resolve N-acetyl derivatives of (DL)-amino acids has been reported by Whitesides and coworkers in *J. Am. Chem. Soc.*, 1989, 111, 6354–6364.

When it is desirable to synthesize these intermediates in optically pure form, established methods include: (1) asymmetric electrophilic amination of chiral enolates (*J. Am. Chem. Soc.*, 1986, 108, 6394–6395, 6395–6397, and 6397–6399), (2) asymmetric nucleophilic amination of optically active carbonyl derivatives, (*J. Am. Chem. Soc.*, 1992, 114, 1906; *Tetrahedron Lett.*, 1987, 28, 32), (3) diastereoselective alkylation of chiral glycine enolate synthons (*J. Am. Chem. Soc.*, 1991, 113, 9276; *J. Org. Chem.*, 1989, 54, 3916), (4) diastereoselective nucleophilic addition to a chiral electrophilic glycinate synthon (*J. Am. Chem. Soc.*, 1986, 108, 1103), (5) asymmetric hydrogenation of prochiral dehydroamino acid derivatives ("*Asymmetric Synthesis, Chiral Catalysis*; Morrison, J. D., Ed; Academic Press: Orlando, Fla., 1985; Vol 5), and (6) enzymatic syntheses (*Angew. Chem. Int. Ed. Engl.*, 1978, 17, 176).

SCHEME 16

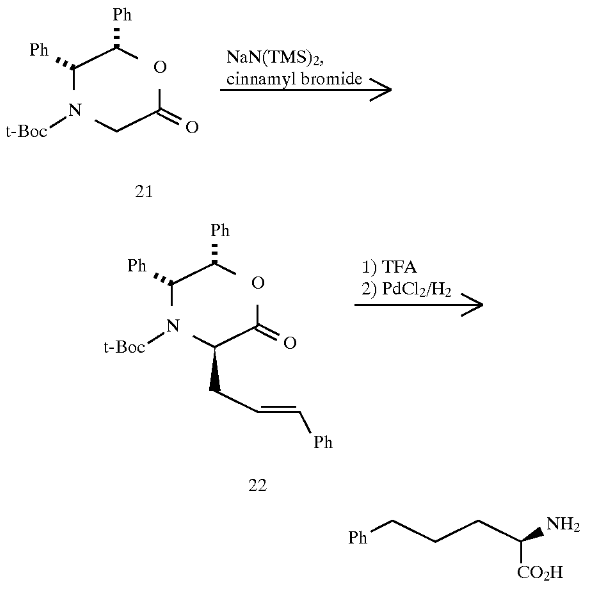

21

22

23

For example, alkylation of the enolate of diphenyloxazinone 21 (*J. Am. Chem. Soc.*, 1991, 113, 9276) with cinnamyl bromide in the presence of sodium bis(trimethylsilyl)amide proceeds smoothly to afford 22 which is converted into the desired (D)-2-amino-5-phenylpentanoic acid 23 by removing the N-t-butyloxycarbonyl group with trifluoroacetic acid and hydrogenation over a $PdCl_2$ catalyst (Scheme 19).

SCHEME 27

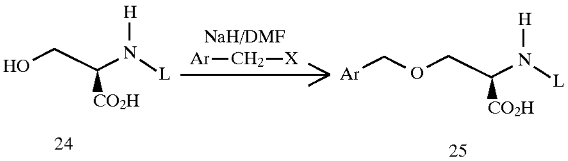

24

25

Intermediates of formula 20 which are O-benzyl-(D)-serine derivatives 25 are conveniently prepared from suitably substituted benzyl halides and N-protected-(D)-serine 24. The protecting group L is conveniently a BOC or a CBZ group. Benzylation of 24 can be achieved by a number of methods well known in the literature including deprotonation with two equivalents of sodium hydride in an inert solvent such as DMF followed by treatment with one equivalent of a variety of benzyl halides (*Synthesis* 1989, 36) as shown in Scheme 17.

The O-alkyl-(D)-serine derivatives may also be prepared using an alkylation protocol. Other methods that could be utilized to prepare (D)-serine derivatives of formula 25 include the acid catalyzed benzylation of carboxyl protected intermediates derived from 24 with reagents of formula $ArCH_2OC(=NH)CCl_3$ (O. Yonemitsu et al., *Chem. Pharm. Bull.*, 1988, 36, 4244). Alternatively, alkylation of the chiral gylcine enolates (*J. Am. Chem. Soc.*, 1991, 113, 9276; *J. Org. Chem.*, 1989, 54, 3916) with $ArCH_2OCH_2X$ where X is a leaving group affords 25. In addition D,L-O-aryl(alkyl) serines may be prepared and resolved by methods described above.

β-Alkyl amino acids can be synthesized well established methods. Some of these methods are documented in J. Samanen et al., *J. Med. Chem.*, 1989, 32, 466, K. Kover et al., *J. Org. chem.*, 1994, 59, 991, V. Hruby et al., *J. Med. Chem.*, 1991, 34, 1823, Y-B. He et al., *J. Am. Chem. Soc.*, 1993, 115, 8066, Z. Huang et al., *J. Am. Chem. Soc.*, 1992, 114, 9390, and D. M. Birney et al., *J. Med. Chem.*, 1995, 38, 2478.

It is noted that in some cases the order of carrying out the foregoing reaction schemes may be varied to facilitate the reaction or to avoid unwanted reaction products.

The utility of the compounds of the present invention as growth hormone secretagogues may be demonstrated by methodology known in the art, such as an assay described by Smith, et al., *Science*, 260, 1640–1643 (1993) (see text of FIG. 2 therein). In particular, the intrinsic growth horomone secretagogue activities of the compounds of the present invention may be demonstrated by this assay. The compounds of the following examples have activity in the aforementioned assay in the range of 0.1 nm to 5 μm.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, to improve feed efficiency and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a corticosteroid to minimize the latter's catabolic side effects or with other pharmaceutically active materials wherein the combination enhances efficacy and minimizes side effects.

Growth promoting and anabolic agents include, but are not limited to, TRH, diethylstilbesterol, amino acids, estrogens, β-agonists, theophylline, anabolic steroids, enkephalins, E series prostaglandins, retinoic acid, compounds disclosed in U.S. Pat. No. 3,239,345, e.g., zeranol, and compounds disclosed in U.S. Pat. No. 4,036,979, e.g., sulbenox. or peptides disclosed in U.S. Pat. No. 4,411,890.

A still further use of the compounds of this invention is in combination with other growth hormone secretagogues such as the growth hormone releasing peptides GHRP-6, GHRP-1 as described in U.S. Pat. No. 4,411,890 and publications WO 89/07110, WO 89/07111 and B-HT920 as well as hexarelin and GHRP-2 as described in WO 93/04081 or growth hormone releasing hormone (GHRH, also designated GRF) and its analogs or growth hormone and its analogs or somatomedins including IGF-1 and IGF-2 or α-adrenergic agonists such as clonidine or serotonin 5HTID agonists such as sumitriptan or agents which inhibit somatostatin or its release such as physostigmine and pyridostigmine. In particular, the compounds of this invention may be used in combination with growth hormone releasing factor, an analog of growth hormone releasing factor, IGF-1, or IGF-2. For example, a compound of the present invention may be used in combination with IGF-1 for the treatment or prevention of obesity. In addition, a compound of this invention may be employed in conjunction with retinoic acid to improve the condition of musculature and skin that results from intrinsic aging.

The present invention is further directed to a method for the manufacture of a medicament for stimulating the release of growth hormone in humans and animals comprising combining a compound of the present invention with a pharmaceutical carrier or diluent.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses may be summarized as follows: stimulating growth hormone release in elderly humans; treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treating obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, and skeletal dysplasia; treatment of hypercortisonism and Cushing's syndrome; treatment of peripheral neuropathies; replacement of growth hormone in stressed patients; treatment of osteochondrodysplasias, Noonans syndrome, sleep disorders, schizophrenia, depression, Alzheimer's disease, delayed wound healing, and psychosocial deprivation; treatment of pulmonary dysfunction and ventilator dependency; prevention or treatment of congestive heart failure, improving pulmonary function, restoring systolic and diastolic function, increasing myocardial contractility, decreasing peripheral total vascular resistance, diminishing or preventing loss of body weight and enhancing recovery following congestive heart failure; increasing appetite; attenuation of protein catabolic response after a major operation; treating malabsorption syndromes; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; stimulation of thymic development and preventtion of the age-related decline of thymic function; adjunctive therapy for patients on chronic hemodialysis; treatment of immunosuppressed patients and to enhance antibody response following vaccination; increasing the total lymphocyte count of a human, in particular, increasing the $T_4/T_8$-cell ratio in a human with a depressed $T_4/T_8$-cell ratio resulting, for example, from infection, such as bacterial or viral infection, especially infection with the human immunodeficiency virus; treatment of syndromes manifested by non-restorative sleep and musculoskeletal pain, including fibromyalgia yndrome or chronic fatigue syndrome; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock; and stimulation of wool growth in sheep. Further, the instant compounds are useful for increasing feed efficiency, promoting growth, increasing milk production and improving the carcass quality of livestock. Likewise, the instant compounds are useful in a method of treatment of diseases or conditions which are benefited by the anabolic effects of enhanced growth hormone levels that comprises the administration of an instant compound.

In particular, the instant compounds are useful in the prevention or treatment of a condition selected from the group consisting of: osteoporosis; catabolic illness; immune deficiency, including that in individuals with a depressed $T_4/T_8$ cell ratio; bone fracture, including hip fracture; musculoskeletal impairment in the elderly; growth hormone deficiency in adults or in children; short stature in children; obesity; sleep disorders; cachexia and protein loss due to chronic illness such as AIDS or cancer; and treating patients recovering from major surgery, wounds or burns, in a patient in need thereof.

In addition, the instant compounds may be useful in the treatment of illnesses induced or facilitated by corticotropin releasing factor or stress- and anxiety-related disorders, including stress-induced depression and headache, abdominal bowel syndrome, immune suppression, HIV infections, Alzheimer's disease, gastrointestinal disease, anorexia nervosa, hemorrhagic stress, drug and alcohol withdrawal symptoms, drug addiction, and fertility problems.

It will be known to those skilled on the art that there are numerous compounds now being used in an effort to treat the diseases or therapeutic indications enumerated above. Combinations of these therapeutic agents some of which have also been mentioned above with the growth hormone secretagogues of this invention will bring additional, complementary, and often synergistic properties to enhance the growth promotant, anabolic and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N. A. T. Role of Bisphosphonates in Metabolic Bone Diseases. *Trends in Endocrinol. Metab.*, 4, 19–25 (1993). Bisphosphonates with these utilities include alendronate, tiludronate, dimethyl—APD, risedronate, etidronate, YM-175, clodronate, pamidronate, and BM-210995. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

In the case of alendronate daily oral dosage levels of 0.1 mg to 50 mg are combined for effective osteoporosis therapy with 0.01 mg/kg to 20 mg/kg of the growth hormone secretagogues of this invention.

Osteoporosis and other bone disorders may also be treated with compounds of this invention in combination with calcitonin, estrogens, raloxifene and calcium supplements such as calcium citrate or calcium carbonate.

Anabolic effects especially in the treatment of geriatric male patients are obtained with compounds of this invention in combination with anabolic steroids such as oxymetholone, methyltesterone, fluoxymesterone and stanozolol.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 10 mg/kg. of body weight daily are administered to patients and animals, e.g., mammals, to obtain effective release of growth hormone. Preferably, the dosage level will be about 0.001 to about 25 mg/kg per day; more preferably about 0.01 to about 10 mg/kg per day.

The following examples are provided for the purpose of further illustration only and are not intended to be limitations on the disclosed invention.

INTERMEDIATE 1

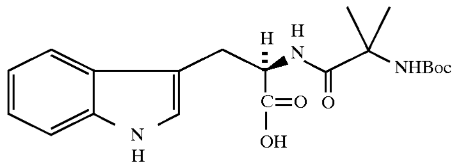

Step A:

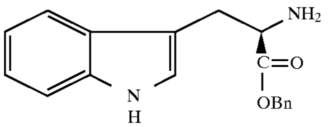

To a solution of the commercially available N-t-BOC-D-tryptophan (25.0 g, 82.2 mmol), benzyl alcohol (10.2 mL, 98.6 mmol), and DMAP (100 mg) in dichloromethane (200 mL) at 0° C., was added EDC (17.4 g, 90.4 mmol) in several portions over a one hour period. The reaction mixture was stirred at room temperature for six hours and was poured into water (200 mL), and the organic layer was separated. The organic solution was washed with a mixture of brine and 3N hydrochloric acid, dried over anhydrous magnesium sulfate, filtered and concentrated to give a thick oil, which solidified upon standing.

To a solution of this oil in 30 mL of dichloromethane was added 20 mL of TFA and stirred for 1 h. The reaction mixture was concentrated, neutralized carefully with saturated aqueous sodium bicarbonate solution, and extracted with dichloromethane (2×100 mnL). The combined organic solution was washed with brine (100 mL), passed through a short column of silica gel eluting with 5–10% methanol in dichloromethane to give 23.2 g of the amine as an oil after evaporation.

Step B:

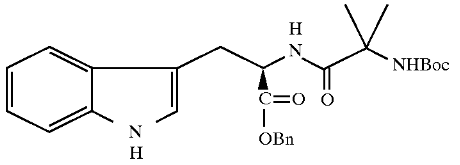

To a solution of the above product, HOBT (10.6 g, 78.8 mmol) and N-BOC-α-methyl alanine (19 g, 94.5 mmol) in 200 mL of dichloromethane, was added EDC (19.5 g, 0.102 mol) in several portions at 0° C. After 5 minutes, the clear reaction mixture became milky. After stirring at room temperature overnight, the reaction mixture was poured into 200 mL of water and the organic layer was separated. The organic solution was washed with brine, and with a brine and saturated sodium bicarbonate solution, dried over anhydrous magnesium sulfate, filtered and concentrated to give a thick oil, which was purified by flash chromatography eluting with 10–40% ethyl acetate in hexane to give the desired material (28.7 g).

$^1$H NMR ($CDCl_3$, 200 MHz) δ 8.48 (br.s, 1H), 7.54 (br.d, 1H), 7.38–7.23 (m, 3H), 7.19 (br.d, 2H), 7.15–7.00 (m, 1H), 6.90 (d, 1H), 6.86 (d, 1H), 5.06 (br.s, 2H), 4.95 (ddd, 1H), 3.30 (2dd, 2H), 1.40 (s, 15H)

Step C:

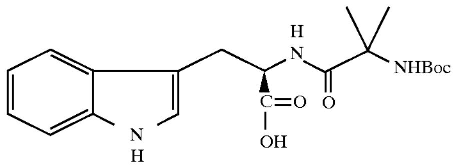

A solution of the material from Step B (28.7 g) in 200 mL of ethanol was stirred at RT under a $H_2$ balloon for 20 minutes in the presence of 10% palladium on carbon (2 g). The catalyst was filtered off through a pad of celite and washed with ethyl acetate. The filtrate was concentrated to give the acid as a slightly pink foam (23.3 g).

$^1$H NMR ($CD_3OD$, 400 MHz) δ 7.56 (d, J=8 Hz, 1H), 7.31 (dd, J=1, 8 Hz, 1H), 7.09 (s, 1H), 7.07 (dt, J=1, 7 Hz, 1H), 6.98 (dt, J=1, 7 Hz, 1H), 4.69 (t, J=6 Hz, 1H), 3.34–3.23 (m, 2H), 1.35 (s, 3H), 1.34 (s, 9H), 1.29 (s, 3H). FAB-MS calc. for $C_{20}H_{27}N_3O_5$: 389; Found 390 (M+H), 290 (M+H-100 (BOC))

INTERMEDIATE 2

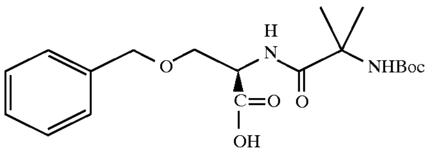

Following the procedures for the preparation of Intermediate 1 using N-t-Boc-O-Benzyl-D-serine in the place of N-t-BOC-D-tryptophan gave Intermediate 2. FAB-MS calc. for $C_{19}H_{28}N_2O_6$: 380; Found 381 (M+H), 325 (M+H-56 (t-Bu)), 281 (M+H-100 (BOC)).

INTERMEDIATE 3

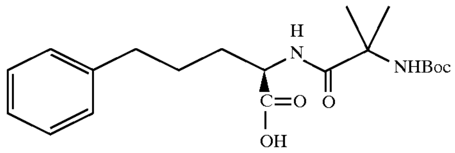

Step A: (DL)-N-Acetyl-2-amino-5-phenylpentanoic acid

To a solution of sodium (2.3 g, 0.1 mol) in ethanol (60 mL) under nitrogen at room temperature, was added diethyl acetamidomalonate. The mixture was stirred at room temperature for one hour, and then 1-bromo-3-phenylpropane was added dropwisely. After the addition, the mixture was stirred at room temperature for two hours, then refluxed overnight. It was cooled to room temperature and partitioned between water and ethyl acetate. The organic layer was washed with sodium bicarbonate in water, dried over MgSO4 and evaporated to give an intermediate (32.5 g, 97%).

$^1$H NMR (CDCl3, 400 MHz) 7.26–7.10 (m, 5H); 6.75 (br. s, 1H); 4.19 (q, J=7 Hz, 4H); 2.58 (t, J=7.9 Hz, 2H); 2.39–2.35 (m, 2H); 2.00 (s, 3H); 1.43–1.39 (m, 2H); 1.20 (t, J=7 Hz, 6H).

The product above was suspended in 190 mL of 2.5N NaOH in water and refluxed for two hours. The mixture was cooled to 0° C., and it was carefully neutralized with 6N HCl to pH2. The precipitate was collected using a glass sinter funnel and washed with a small amount of cold water and air dried. The solid was then suspended in 300 mL of water and refluxed for four hours. The solution was cooled and acidified to pH1 and the solid was collected by filtration (15.3 g, 67%).

$^1$H NMR (CD3OD, 400 MHz) 7.26–7.12 (m, 5H); 4.90–4.37 (m, 1H); 2.65–2.60 (m, 2H); 1.97 (s, 3H); 1.87–1.82 (m, 1H); 1.73–1.65 (m, 3H).

Step B: (D)-N-Acetyl-2-amino-5-phenylpentanoic acid

The racemic intermediate from the previous step (10 g, 42.5 mmol) and CoCl3-6$H_2$O were dissolved in 21 ml of 2N KOH and 200 mL of water at 40° C., and the pH of the solution was adjusted to 8 by the addition of the several drops of 2N KOH. Then acylase I (Aspergillus sp, 0.5 u/mg, from Sigma; 0.9 g) was added with vigorous stirring. The reaction mixture was stirred for one day at 40° C. and the pH was kept at 8 by the addition of a few drops of KOH. The solid which formed was filtered off. The filtrate was acidified by 3N HCl to pH2, and was extracted with ethyl acetate (200 mL×4). The organic extracts were combined and evaporated to give a white solid (4.64 g, 46%)

$^1$H NMR (CD3OD, 400 MHz) 7.26–7.12 (m, 5H); 4.90–4.37 (m, 1H); 2.65–2.60 (m, 2H); 1.97 (s, 3H); 1.87–1.82 (m, 1H); 1.73–1.65 (m, 3H).

Step C: (D)-N-t-Boc-2-amino-5-phenylpentanoic acid

The intermediate from step B (4.2 g, 17.8 mmol) was suspended in 2N HCl (100 mL) and refluxed for two hours. The reaction mixture was evaporated in vacuo to remove water and hydrochloric acid to yield a white solid. To a solution of this solid in 50 mL of water, was added 3N NaOH until the pH 11, then di-t-butyl dicarbonate (4.66 g, 21.4 mmol) was added with vigorous stirring. After four hours, the reaction mixture was acidified to pH2 with 3N HCl and it was extracted with ethyl acetate (100 mL×3). The organic extracts were combined and evaporated to give a white solid (6.56 g, crude) which was used without purification. $^1$H NMR (CD3OD, 400 MHz) 7.26–7.12 (m, 5H); 4.11–4.08 (m, 1H); 2.65–2.60 (m, 2H); 1.83–1.62 (m, 4H); 1.43 (s, 9H).

Step D:

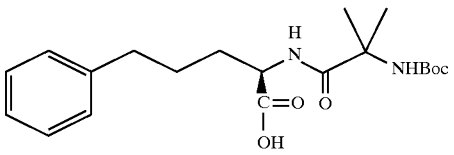

Following the procedures for the preparation of Intermediate 1 using (D)-N-t-Boc-2-amino-5-phenylpentanoic acid in the place of N-t-BOC-D-tryptophan gave Intermediate 3. $^1$H NMR ($CDCl_3$, 400 MHz) 7.24–7.20 (m, 2H), 7.15–7.04 (m, 3H), 4.60–4.55 (m, 1H), 2.62–2.55 (m, 2H), 2.00–1.86 (m, 1H), 1.78–1.60 (m, 3H), 1.50 (s, 6H), 1.30 (s, 9H).

EXAMPLE 1

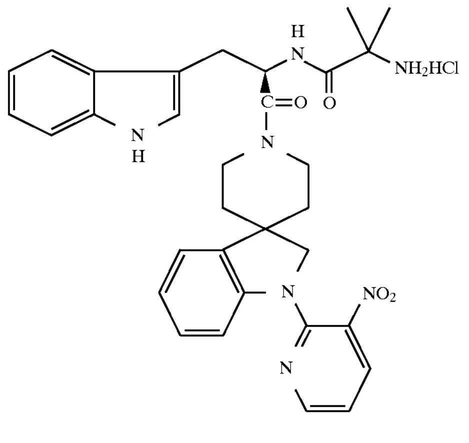

Step A:

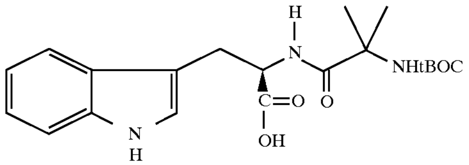

To 5.0 g (16.5 mmol) of the commercially available N-t-BOC-D-tryptophan in 100 mL of chloroform was added 1.80 mL (16.5 mmol) of benzyl alcohol, 0.20 g (1.65 mmol) of 4-N,N-dimethylamino pyridine (DMAP), and 3.20 g of EDC and stirred for 16 h. The reaction mixture was poured into 100 mL of water and the organic layer was separated. The aqueous was further extracted with 2×100 mL of chloroform. The combined organics were washed with 50 mL of 10% aqueous citric acid, 100 mL of 10% aqueous sodium bicarbonate solution, dried over anhydrous magnesium sulfate, filtered and concentrated to give a thick oil.

To a solution of this oil in 10 mL of dichloromethane was added 20 mL of trifluoroacetic acid and stirred for 1 h. The reaction mixture was concentrated, basified carefully with saturated aqueous sodium bicarbonate solution, and extracted with chloroform (2×100 mL). The combined organics were washed with brine (100 mL), dried over potassium carbonate, filtered, and concentrated to give 5.46 g of the amine as a brown oil which was used without purification.

To 5.46 g of the above product in 100 mL of chloroform was added 3.40 g (22.2 mmol) of HOBT, 4.60 g (22.2 mmol) of N-BOC-α-methyl alanine, and 5.32 g (28.0 mmol) of EDC and stirred for 16 h. The reaction mixture was poured into 100 mL of water and the organic layer was separated. The aqueous was further extracted with 2×100 mL of chloroform. The combined organics were washed with 50 mL of 10% aqueous citric acid, 100 mL of 10% aqueous sodium bicarbonate solution, dried over anhydrous magnesium sulfate, filtered and concentrated to give 6.94 g of the product as a thick oil. Flash chromatography (200 g $SiO_2$; hexane-ethyl acetate as eluent) gave 4.75 g of the desired material as a colorless foam.

$^1$H NMR ($CDCl_3$, 200 MHz) δ 8.48 (bs, 1H), 7.54 (bd, 1H), 7.38–7.23 (m, 3H), 7.19 (bd, 2H), 7.15–7.00 (m, 1H), 6.90 (d, 1H), 6.86 (d, 1H), 5.06 (bs, 2H), 4.95 (ddd, 1H), 3.30 (2dd, 2H), 1.40 (s, 15H)

To a solution of 4.75 g of the material from Step B in 100 mL of ethanol was added 1.0 g of 10% Pd/C and stirred at RT under a $H_2$ balloon for 18 h. The catalyst was filtered off through a pad of celite and washed with ethyl acetate. The filtrate was concentrated to give 2.96 g of the acid as a colorless foam.

$^1$H NMR ($CDCl_3$, 200 MHz) δ 8.60 (bs, 1H), 7.55 (d, 1H), 7.26–6.90 (m, 3H), 6.88 (bd, 1H), 4.80 (m, 1H), 3.32 (2dd, 2H), 1.37 (s, 3H), 1.35 (s, 12H)

Step B:

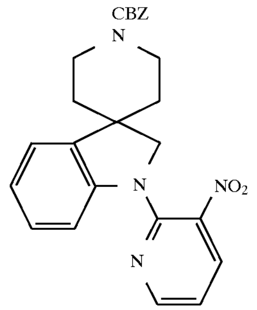

To a solution of 0.40 g of 1'-benzyloxycarbonyl-1,2-dihydro-spiro[3H-indole-3,4'-piperdine] in 10 mL of dry DMF was added 0.25 g of 2-chloro-3-nitropyridine, 0.50 g of powdered potassium carbonate and heated at 100° C. overnight. The reaction mixture was cooled to room temperature, diluted with water and extracted with ethyl acetate. The combined organics were washed with $NaHCO_3$ solution, brine and dried over anhydrous $K_2CO_3$ and concentrated to give reddish-brown residue that was used without purification.

Step C:

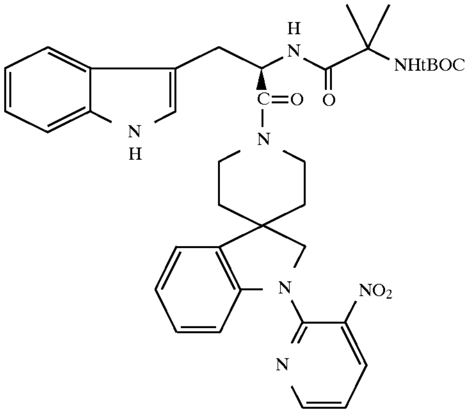

This material from Step B was treated with 1 mL of HBr in acetic acid for 1 h. The precipitate was filtered and washed with ether. The precipitate was suspended in dichloromethane and basified with 1N NaOH till the pH=10. The organic layer was separated, washed with brine, dried over $Na_2SO_4$ and concentrated. The piperidine intermediate was coupled with the intermediate synthesized in Step A under standard peptide-type coupling conditions and isolated after standard work-up and purification by flash chromatography with hexane-acetone (2:1) as the eluent. FAB MS calcd. for $CC_{37}H_{43}N_7O_6$ 681; found 682.3

Step D:

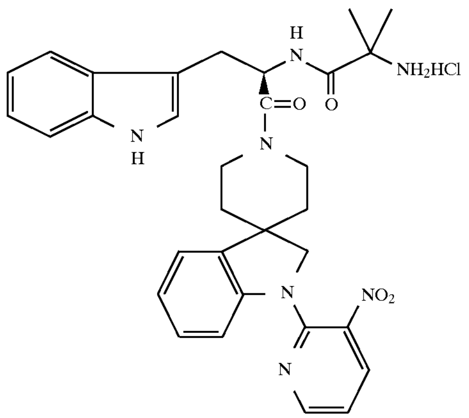

The intennediate prepared in Step A (50 mg) was treated with a saturated solution of HCl (gas) in ethyl acetate for 30 minutes. Ether was added and the precipitate was collected and dried. The title compound was a yellow solid. FAB MS calcd. for $C_{32}H_{37}N_7O_4$ 581; found 582.4

EXAMPLE 2

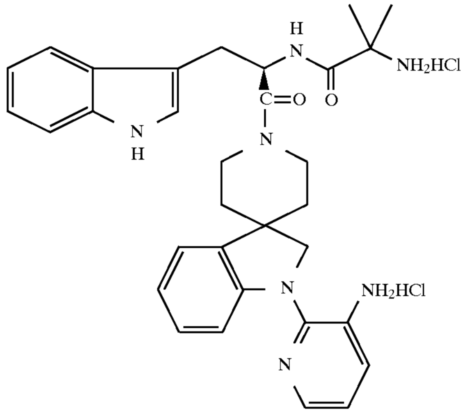

Approximately 0.10 g of the intermediate prepared in Step C of Example was hydrogenated at 40 psi in ethanol with Raney nickel as the catalyst for 18 h. The catalyst was filtered off the filtrate was concentrated to give the amino-pyridine. The BOC protecting group was removed by the HCl lethylacetate procedure to give the title compound as an orange solid. FAB MS calcd. for $C_{32}H_{37}N_7O_2$ 551; found 552.6.

EXAMPLE 3

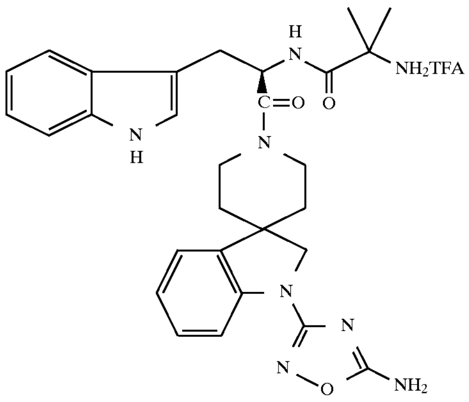

Step A:

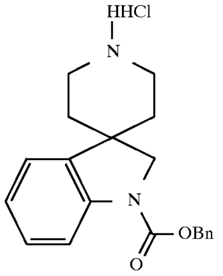

To a solution of 1'-methyl-1,2-dihydro-spiro[3H-indole-3,4'-piperdine] (Prepared as described in H. Ong et al., *J. Med. Chem.*, 1983, 23, 981–986) in $CH_2Cl_2$ at 0° C. was added triethylamine and CBZ-Cl and stirred for 1 h at RT. The reaction mixture was poured into 5% HCl and the aqueous layer was separated. The aqueous layer was basified with 50% NaOH to pH=10 and extracted with $CH_2Cl_2$. The combined organics were washed with brine, dried over $K_2C_3$, and concentrated to yield the desired compound as a thick oil.

To a solution of above product in dry 1,2-dichloroethane at 0° C. was added 1-chloroethyl chloroformate, and then stirred at RT for 30 min and finally at reflux for 1 h. The reaction mixture was concentrated to approximately one third of the volume and then diluted with dry methanol and refluxed for 1.5 h. The reaction was cooled to RT and concentrated to approximately one half of the volume. The precipitate was filtered and washed with a small volume of cold methanol. This yielded the piperidine HCl salt as a white solid. This material was used without purification.

Step B:

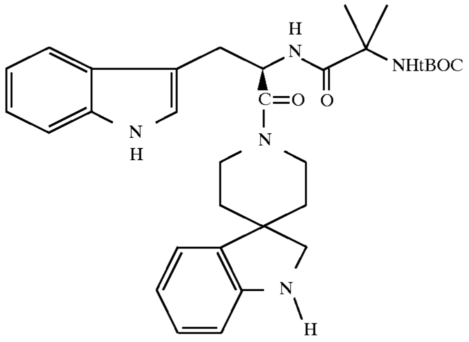

To a solution of 4.2 g of N-tBOC-(D)-tryptophan in 50 mL of dichloromethane was added 5 g of the above piperidine hydrochloride, 3.08 mL of N-methylmorpholine, 1.90 g of HOBT and 2.80 g of EDC and stirred at room temperature for 18 h. The reaction mixture was washed with 0.1N HCl (50 mL), saturated aqueous $NaHCO_3$ solution, dried over MgSO4 and concentrated to give an oily residue that was dissolved in 10 mL of dichloromethane and treated with 15 mL of TFA for 30 min. The volatiles were removed at reduced pressure and the residue was taken up in 50 mL of chloroform and basified with saturated sodium carbonate solution till pH=9. The oraganic layer was separated, washed with brine, dried over $K_2CO_3$ and concentrated. This amine compound was coupled with 14.0 mmol of N-tBOC-AIB by using the above coupling procedure. This coupled product was taken up in 25 mL of ethanol and hydrogenated at 40 psi on a Parr shaker with 1 g of 10% Pd/C as the catalyst for 16 h to give the desired material (crude), after filtration of the reaction mixture and concentration of the filtrate, as a fluffy solid. This material was used without purification.

Step C:

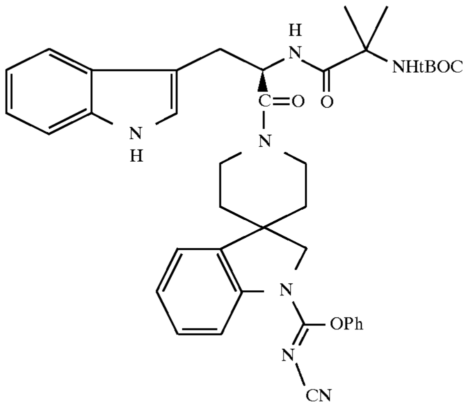

To 1.65 g of the spiroindoline intermediate from Step B in 100 mL of iso-propanol was added 0.72 g of N-cyanodiphenoxy-imidocarbonate and stirred at room temperature overnight. The volatiles were removed on the rotary evaporator and the resulting solid was purified by column chromatography with ether-dichloromethane (1:1 to 7:3) as the eluent to give 1.26 g of the desired material as a colorless solid.

Step D:

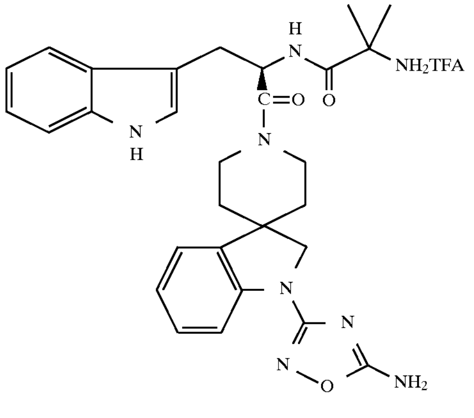

Approximately 0.2 g of the intermediate from Step C in 10 mL of methanol was added a solution 0.085 mL of 5N NaOH solution and 0.029 g of hydroxylamine hydrochloride in methanol and the reaction was stirred at rt for 5 h. The solvent was removed under reduced pressure, the residue was re-dissolved in water and extracted with dichloromethane. The combined organics were dried over $MgSO_4$, concentrated and the residue was purified by rotary chromatography (2% methanol in dichloromethane to 5% methanol in dichloromethane) to the desired product as a white solid.

The 0.030 g of above BOC compound was added 1 mL of 50% trifluoroacetic acid in dichloromethane and stirred for 30 min. The reaction mixture was concentrated to dryness to give the title compound as a solid. FAB MS calcd. for $C_{29}H_{34}N_8O_3$ 542.6; found 543.2 (m+1).

EXAMPLE 4

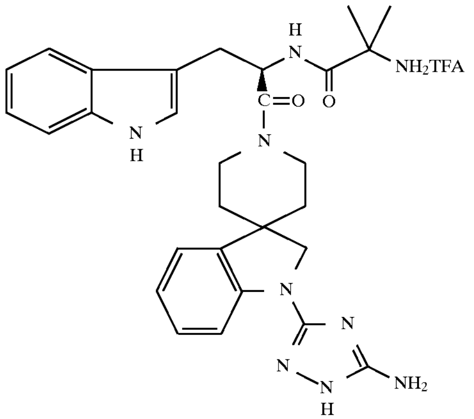

The title compound was prepared as described in Example 3 Step D but hydrazine hydrate was used in place of hydroxylamine. Key resonances in 400 MHz $^1$H NMR ($CD_3OD$, mixture of rotamers) 7.80–7.50 (m, 2H), 6.50–6.40 (d, 1H), 5.30–5.15 (m, 1H), 4.50–4.30 (m, 1H), 3.30–3.10 (m, 2H), 1.55–1.40 (4s, 6H), 1.10–0.80 (m, ½H), 0.20–0.0 (m, ½H). FAB MS calcd. for $C_{29}H_{35}N_9O_2$ 541.6; found 542.2 (m+1).

EXAMPLE 5

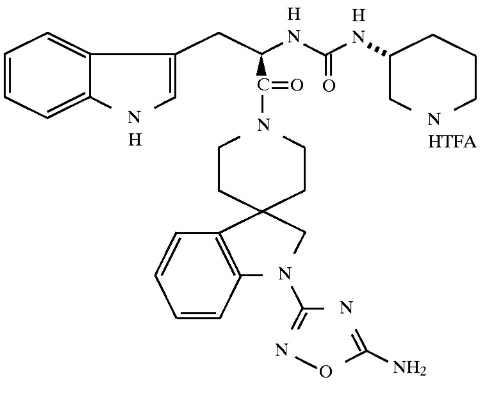

This material was synthesized in an analogous manner to the compound prepared in Example 3 but the requisite (R)-N-tBOC piperidinyl isocyanate (prepared by Curtius rearrangement of (R)-NtBOC nipecotic acid) was used in Step C to prepare the urea. Elaboration of the heterocycle and the final deblock of the BOC protecting group proceeded without any difficulties. Key resonances in 400 MHz $^1$H NMR ($CD_3OD$, mixture of rotamers) 7.80–7.50 (m, 2H), 7.20–6.80 (m, 6H), 6.50 (d, 1H), 5.5–5.20 (m, 1H), 4.50–4.30 (m, 1H), 3.80–3.50 (m, 7H), 3.30–3.10 (m, 3H), 1.10–1.00 (m, ½H), 0.20 (bt, ½H).

EXAMPLE 6

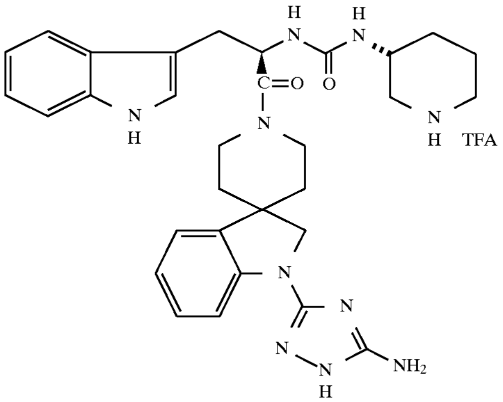

This material was synthesized in an analogous manner to the compound prepared in Example 4 but the requisite (R)-N-tBOC piperidinyl isocyanate (prepared by Curtius rearrangement of (R)-NtBOC nipecotic acid) was used in Step C of Example 3 to prepare the urea. Elaboration of the heterocycle and the final deblock of the BOC protecting group proceeded without any difficulties. Key resonances in 400 MHz $^1$H NMR ($CD_3OD$, mixture of rotamers) 7.80–7.50 (m, 2H), 7.20–6.80 (m, 6H), 6.50 (d, 1H), 5.5–5.20 (m, 1H), 4.50–4.30 (m, 1H), 3.80–3.50 (m, 7H), 3.30–3.10 (m, 3H), 1.10–1.00 (m, ½H), 0.20 (bt, ½H). FAB MS calcd. for $C_{31}H_{28}N_{10}O_2$ 582.7; found 583.4 (m+1).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula:

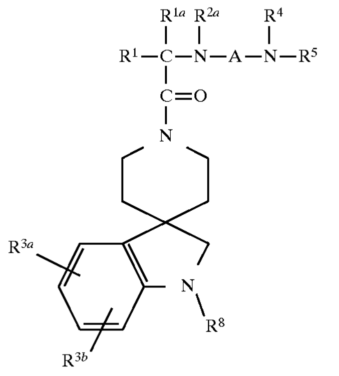

wherein:

$R^1$ is selected from the group consisting of:

$C_1$–$C_{10}$ alkyl, -aryl-, aryl ($C_1$–$C_6$ alkyl)-, heteroaryl-, heteroaryl($C_1$–$C_6$ alkyl)-, ($C_3$–$C_7$ cycloalkyl)-($C_1$–$C_6$ alkyl)-, ($C_1$–$C_5$ alkyl)-K-($C_1$–$C_5$ alkyl)-, aryl-($C_0$–$C_5$ alkyl)-K-($C_1$–$C_5$ alkyl)-, heteroaryl-($C_0$–$C_5$ alkyl)-K-($C_1$–$C_5$ alkyl)-, and ($C_3$–$C_7$ cycloalkyl)-($C_0$–$C_5$ alkyl)-K-($C_1$–$C_5$ alkyl)-, wherein K is —O—, —$S(O)_m$—, —$N(R^2)C(O)$—, —$C(O)N(R^2)$—, —OC(O)—, —C(O)O—, —$CR^2$=$CR^2$— or —C≡C—, wherein $R^2$ and alkyl may be further substituted with 1 to 9 halo, —$S(O)_mR^{2a}$, 1 to 3 of —$OR^{2a}$, or —$C(O)OR^{2a}$, and wherein aryl is phenyl or naphthyl, and heteroaryl is indolyl, wherein aryl and heteroaryl are unsubstituted or substituted with phenyl, phenoxy, halophenyl, 1 to 3 of -$C_1$–$C_6$ alkyl, 1 to 3 of halo, 1 to 2 of —$OR^2$, methylenedioxy, —$S(O)_mR^2$, 1 to 2 of —$CF_3$, —$OCF_3$, nitro, —$N(R^2)(R^2)$, —$N(R^2)C(O)(R^2)$, —$C(O)OR^2$, —$C(O)N(R^2)(R^2)$, —$SO_2N(R^2)(R^2)$, —$N(R^2)SO_2$-aryl, or —$N(R^2)SO_2R^2$;

$R^{1a}$ is hydrogen or $C_1$–$C_4$ alkyl;

$R^2$ is selected from the group consisting of:

hydrogen, -$C_1$–$C_6$ alkyl, -$C_3$–$C_7$ cycloalkyl, and —$CH_2$-phenyl, wherein the alkyl or the cyloalkyl is unsubstituted or substituted with a substituent selected from: hydroxyl, $C_1$–$C_3$ alkoxy, thioalkyl, and $C(O)OR^{2a}$, and wherein if two -$C_1$–$C_6$ alkyl groups are present on one atom, the groups may be optionally joined to form a $C_3$–$C_8$ cyclic ring selected from the group consisting of pyrrolidine, piperidine, piperazine, morpholine, and thiomorpholine;

$R^{2a}$ is hydrogen or $C_1$–$C_6$ alkyl;

$R^{3a}$ and $R^{3b}$ are independently selected from:

hydrogen, phenyl, phenoxy, halophenyl, -$C_1$–$C_6$ alkyl, halo, —$OR^2$, methylenedioxy, —$S(O)_mR^2$, —$CF_3$, —$OCF_3$, nitro, —$N(R^2)(R^2)$, —$N(R^2)C(O)(R^2)$, —$C(O)OR^2$, —$C(O)N(R^2)(R^2)$, —$SO_2N(R^2)(R^2)$, —$N(R^2)SO_2$-aryl, and —$N(R^2)SO_2R^2$;

$R^4$ is independently hydrogen, $C_1$–$C_6$ alkyl or substituted $C_1$–$C_6$ alkyl where the substituents are selected from 1 to 5 halo, 1 to 3 hydroxy, phenyl, and $C_1$–$C_6$ alkoxycarbonyl;

$R^5$ is selected from the definitions of $R^4$;

A is:

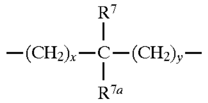 or 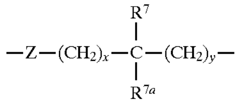

where Z is —$N(R^6)$— or —O—, where $R^{6a}$ is hydrogen or $C_1$–$C_6$ alkyl;

$R^7$ and $R^{7a}$ are independently selected from:

hydrogen, $C_1$–$C_6$ alkyl, trifluoromethyl, phenyl, and substituted $C_1$–$C_6$ alkyl where the substituents are selected from: imidazolyl, naphthyl, phenyl, indolyl, p-hydroxyphenyl, —$OR^2$, —$S(O)_mR^2$, —$C(O)OR^2$, $C_3$–$C_7$ cycloalkyl, —$N(R^2)(R^2)$, —$C(O)N(R^2)(R^2)$, or $R^7$ and $R^{7a}$ may independently be joined to one or both of $R^4$ group to form an alkylene bridge between the terminal nitrogen and the alkyl portion of the $R^7$ or $R^{7a}$ groups, wherein the bridge contains 1 to 5 carbons atoms, or $R^7$ and $R^{7a}$ can be joined to one another to form $C_3$–$C_7$ cycloalkyl;

$R^8$ is heteroaryl, wherein the heteroaryl is optionally substituted with substituents selected from the group consisting of:

hydrogen, phenyl, phenoxy, halophenyl, -$C_1$–$C_6$ alkyl, halo, —$OR^2$, methylenedioxy, —$S(O)_mR^2$, —$CF_3$, —$OCF_3$, nitro, —$N(R^2)(R^2)$, —$N(R^2)C(O)(R^2)$, —$C(O)OR^2$, —$C(O)N(R^2)(R^2)$, —$SO_2N(R^2)(R^2)$, —$N(R^2)SO_2$-aryl, or —$N(R^2)SO_2R^2$ and wherein heteroaryl is selected from the group consisting of: oxadiazole, triazole, pyridine, thiadiazole, dioxathiadiazole, pyrazine, pyrimidine, thiophene, thiadiazole, thiazole, imidazole, and tetrazole;

m is 0, 1, or 2;

x and y are independently 0, 1, 2 or 3;

or a pharmaceutically acceptable salt or an individual diastereomer thereof.

2. The compound of claim 1 of the formula:

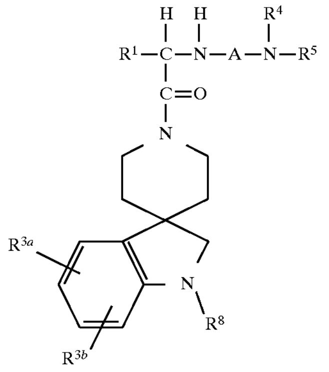

wherein:

$R^1$ is selected from the group consisting of:

$C_1$–$C_{10}$ alkyl, -aryl-, aryl ($C_1$–$C_6$ alkyl)-, heteroaryl-, heteroaryl($C_1$–$C_6$ alkyl)-, ($C_3$–$C_7$ cycloalkyl)-($C_1$–$C_6$ alkyl)-, ($C_1$–$C_5$ alkyl)-K-($C_1$–$C_5$ alkyl)-, aryl-($C_0$–$C_5$ alkyl)-K-($C_1$–$C_5$ alkyl)-, heteroaryl-($C_0$–$C_5$ alkyl)-K-($C_1$–$C_5$ alkyl)-, and ($C_3$–$C_7$ cycloalkyl)-($C_0$–$C_5$ alkyl)-K-($C_1$–$C_5$ alkyl)-, wherein K is —O—, —$S(O)_m$—, —$N(R^2)C(O)$—, —$C(O)N(R^2)$—, —OC(O)—, —C(O)O—, —$CR^2$═$CR^2$— or —C≡C—, wherein $R^2$ and alkyl may be further substituted with 1 to 9 halo, —$S(O)_mR^{2a}$, 1 to 3 of —$OR^{2a}$, or —$C(O)OR^{2a}$, and wherein aryl is phenyl or naphthyl, and heteroaryl is indolyl, wherein aryl and heteroaryl are unsubstituted or substituted with phenyl, phenoxy, halophenyl, 1 to 3 of -$C_1$–$C_6$ alkyl, 1 to 3 of halo, 1 to 2 of —$OR^2$, methylenedioxy, —$S(O)_mR^2$, 1 to 2 of —$CF_3$, —$OCF_3$, nitro, —$N(R^2)(R^2)$, —$N(R^2)C(O)(R^2)$, —$C(O)OR^2$, —$C(O)N(R^2)(R^2)$, —$SO_2N(R^2)(R^2)$, —$N(R^2)SO_2$-aryl, or —$N(R^2)SO_2R^2$;

$R^2$ is selected from the group consisting of:

hydrogen, -$C_1$–$C_6$ alkyl, -$C_3$–$C_7$ cycloalkyl, and —$CH_2$-phenyl, wherein the alkyl or the cyloalkyl is unsubstituted or substituted with a substituent selected from: hydroxyl, $C_1$–$C_3$ alkoxy, thioalkyl, and $C(O)OR^{2a}$, and wherein if two -$C_1$–$C_6$ alkyl groups are present on one atom, the groups may be optionally joined to form a $C_3$–$C_8$ cyclic ring selected from the group consisting of pyrrolidine, piperidine, piperazine, morpholine, and thiomorpholine;

$R^{3a}$ and $R^{3b}$ are independently selected from:

hydrogen, phenyl, phenoxy, halophenyl, -$C_1$–$C_6$ alkyl, halo, —$OR^2$, methylenedioxy, —$S(O)_mR^2$, —$CF_3$, —$OCF_3$, nitro, —$N(R^2)(R^2)$, —$N(R^2)C(O)(R^2)$, —$C(O)OR^2$, —$C(O)N(R^2)(R^2)$, —$SO_2N(R^2)(R^2)$, —$N(R^2)SO_2$-aryl, and —$N(R^2)SO_2R^2$;

$R^4$ is independently hydrogen, $C_1$–$C_6$ alkyl or substituted $C_1$–$C_6$ alkyl where the substituents are selected from 1 to 5 halo, 1 to 3 hydroxy, phenyl, and $C_1$–$C_6$ alkoxycarbonyl;

$R^5$ is selected from the definitions of $R^4$;

A is:

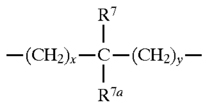 or 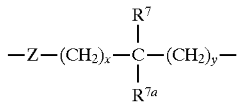

where Z is —$N(R^{6a})$— or —O—, where $R^{6a}$ is hydrogen or $C_1$–$C_6$ alkyl;

$R^7$ and $R^{7a}$ are independently selected from:

hydrogen, $C_1$–$C_6$ alkyl, trifluoromethyl, phenyl, and substituted $C_1$–$C_6$ alkyl where the substituents are selected from: imidazolyl, naphthyl, phenyl, indolyl, p-hydroxyphenyl, —$OR^2$, —$S(O)_mR^2$, —$C(O)OR^2$, $C_3$–$C_7$ cycloalkyl, —$N(R^2)(R^2)$, —$C(O)N(R^2)(R^2)$, or $R^7$ and $R^{7a}$ may independently be joined to one or both of $R^4$ group to form an alkylene bridge between the terminal nitrogen and the alkyl portion of the $R^7$ or $R^{7a}$ groups, wherein the bridge contains 1 to 5 carbons atoms, or $R^7$ and $R^{7a}$ can be joined to one another to form $C_3$–$C_7$ cycloalkyl;

$R^8$ is heteroaryl, wherein the heteroaryl is optionally substituted with substituents selected from the group consisting of:

hydrogen, phenyl, phenoxy, halophenyl, -$C_1$–$C_6$ alkyl, halo, —$OR^2$, methylenedioxy, —$S(O)_mR^2$, —$CF_3$, —$OCF_3$, nitro, —$N(R^2)(R^2)$, —$N(R^2)C(O)(R^2)$, —$C(O)OR^2$, —$C(O)N(R^2)(R^2)$, —$SO_2N(R^2)(R^2)$, —$N(R^2)SO_2$-aryl, or —$N(R^2)SO_2R^2$ and wherein heteroaryl is selected from the group consisting of: oxadiazole, triazole, pyridine, thiadiazole, dioxathiadiazole, and tetrazole;

m is 0, 1, or 2;

x and y are independently 0, 1, 2 or 3;

or a pharmaceutically acceptable salt or an individual diastereomer thereof.

3. A compound which is selected from the group consisting of:

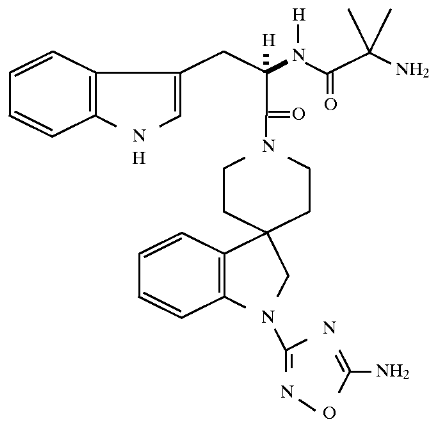

-continued
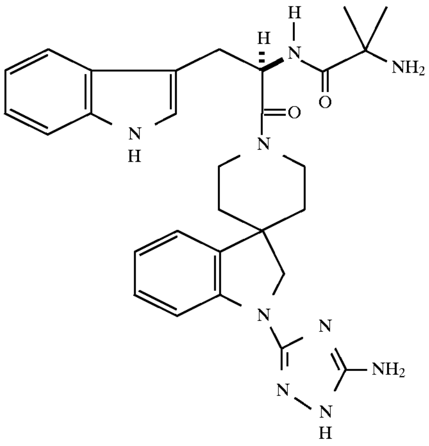
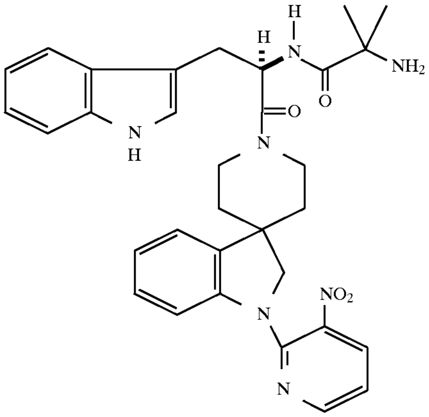
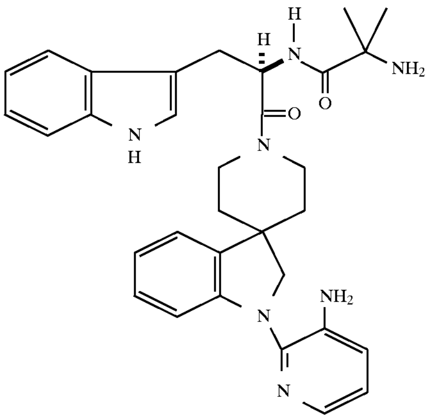
-continued
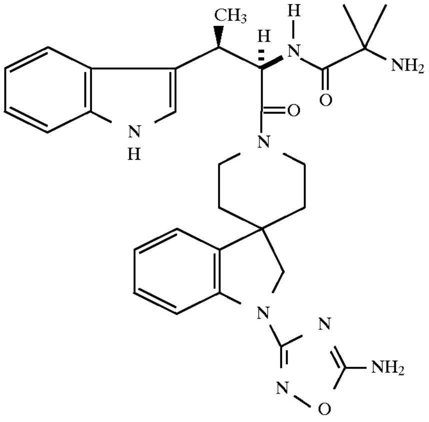
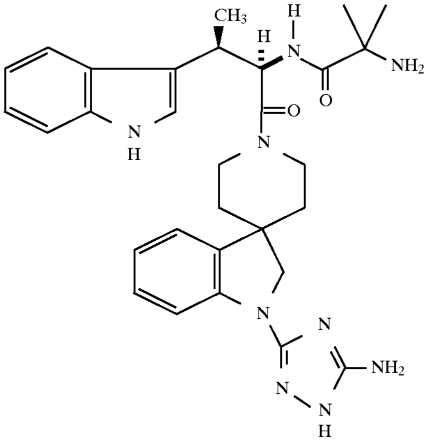
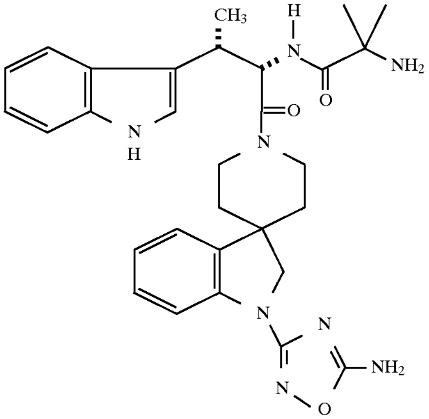

-continued
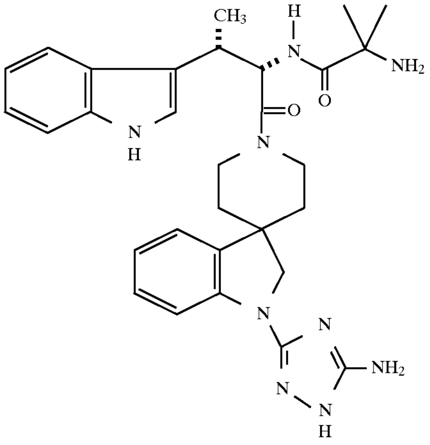
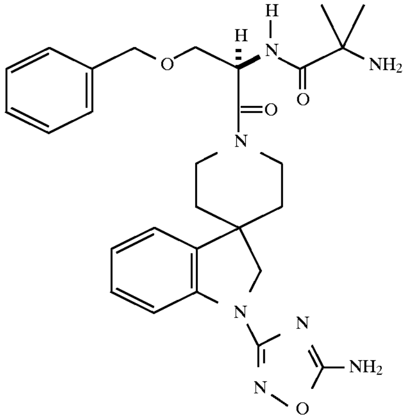
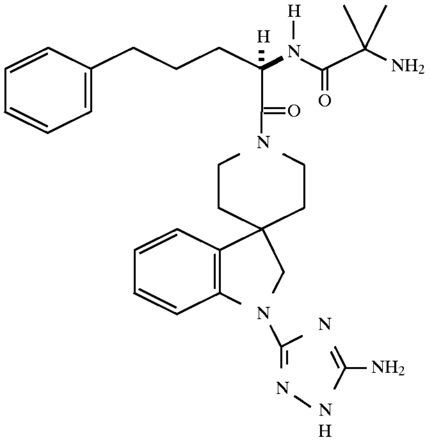
-continued
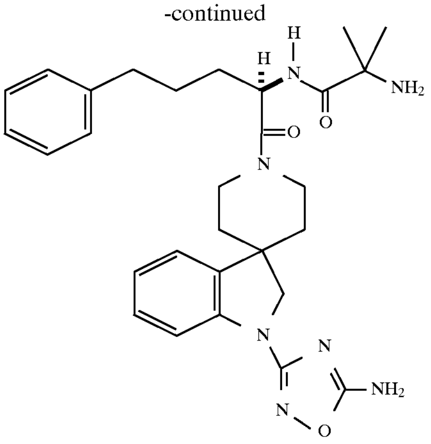
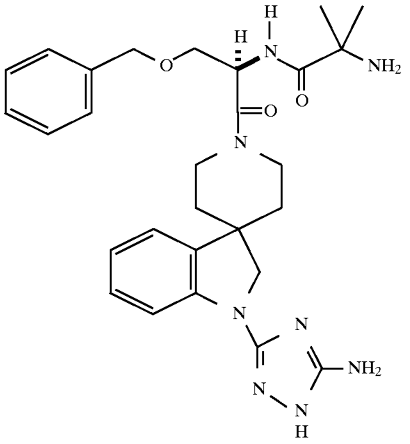
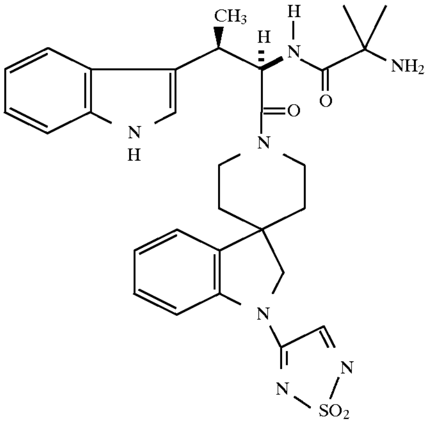
and pharmaceutically acceptable salts and individual diastereomers thereof.
4. A pharmaceutical composition which comprises an inert carrier and an effective amount of a compound of claim 1.
* * * * *